(12) United States Patent
Gunther et al.

(10) Patent No.: US 11,957,595 B2
(45) Date of Patent: Apr. 16, 2024

(54) METHODS AND DEVICES FOR LESS INVASIVE GLENOID REPLACEMENT

(71) Applicant: Shoulder Innovations, Inc., Holland, MI (US)

(72) Inventors: Stephen B. Gunther, Charlottesville, VA (US); Desmond O'Farrell, Grand Rapids, MI (US); Mark Edwin Zyzelewski, Kalamazoo, MI (US); Andrew John Rodenhouse, Grand Rapids, MI (US)

(73) Assignee: Shoulder Innovations, Inc., Holland, MI (US)

( * ) Notice: Subject to any disclaimer, the term of this patent is extended or adjusted under 35 U.S.C. 154(b) by 0 days.

(21) Appl. No.: 18/058,165

(22) Filed: Nov. 22, 2022

(65) Prior Publication Data

US 2023/0078024 A1 Mar. 16, 2023

Related U.S. Application Data

(63) Continuation of application No. 17/027,493, filed on Sep. 21, 2020, which is a continuation of application
(Continued)

(51) Int. Cl.
*A61F 2/40* (2006.01)
*A61B 17/15* (2006.01)
(Continued)

(52) U.S. Cl.
CPC ............ *A61F 2/4081* (2013.01); *A61B 17/15* (2013.01); *A61B 17/1659* (2013.01); *A61B 17/1684* (2013.01); *A61B 17/86* (2013.01); *A61B 17/8802* (2013.01); *A61B 17/8808* (2013.01); *A61F 2/30749* (2013.01); *A61F 2/30771* (2013.01); *A61F 2/4059* (2013.01); *A61F 2/4684* (2013.01); *A61B 17/00234* (2013.01); *A61B 2017/8813* (2013.01);
(Continued)

(58) Field of Classification Search
CPC ....... A61F 2/40; A61F 2/4081; A61F 2/30771
See application file for complete search history.

(56) References Cited

U.S. PATENT DOCUMENTS

| 2,781,758 A | 2/1957 | Jacques |
| 3,979,778 A | 9/1976 | Stroot |

(Continued)

FOREIGN PATENT DOCUMENTS

| DE | 4220217 | 12/1993 |
| DE | 10164328 A1 | 7/2003 |

(Continued)

OTHER PUBLICATIONS

US 11,672,669 B2, 06/2023, Running et al. (withdrawn)
(Continued)

*Primary Examiner* — Brian A Dukert
(74) *Attorney, Agent, or Firm* — Knobbe, Martens, Olson & Bear, LLP

(57) ABSTRACT

The invention relates to a glenoid (shoulder socket) implant prosthesis, a humeral implant prosthesis, devices for implanting glenoid and humeral implant prostheses, and less invasive methods of their use for the treatment of an injured or damaged shoulder.

10 Claims, 39 Drawing Sheets

Related U.S. Application Data

No. 15/477,316, filed on Apr. 3, 2017, now Pat. No. 10,779,952, which is a continuation of application No. 14/329,853, filed on Jul. 11, 2014, now Pat. No. 9,610,166, which is a continuation of application No. 12/719,182, filed on Mar. 8, 2010, now Pat. No. 8,778,028, which is a continuation-in-part of application No. 11/066,978, filed on Feb. 25, 2005, now Pat. No. 8,007,538.

(51) Int. Cl.
*A61B 17/16* (2006.01)
*A61B 17/86* (2006.01)
*A61B 17/88* (2006.01)
*A61F 2/30* (2006.01)
*A61F 2/46* (2006.01)
*A61B 17/00* (2006.01)

(52) U.S. Cl.
CPC ............... *A61F 2002/30112* (2013.01); *A61F 2002/30113* (2013.01); *A61F 2002/30118* (2013.01); *A61F 2002/30125* (2013.01); *A61F 2002/30153* (2013.01); *A61F 2002/3023* (2013.01); *A61F 2002/30332* (2013.01); *A61F 2002/30574* (2013.01); *A61F 2002/30579* (2013.01); *A61F 2002/30606* (2013.01); *A61F 2002/30609* (2013.01); *A61F 2002/30617* (2013.01); *A61F 2002/30657* (2013.01); *A61F 2002/3069* (2013.01); *A61F 2/30767* (2013.01); *A61F 2002/3079* (2013.01); *A61F 2002/30818* (2013.01); *A61F 2002/3082* (2013.01); *A61F 2002/30822* (2013.01); *A61F 2002/30823* (2013.01); *A61F 2002/30827* (2013.01); *A61F 2002/30878* (2013.01); *A61F 2002/30884* (2013.01); *A61F 2002/30934* (2013.01); *A61F 2/40* (2013.01); *A61F 2002/4033* (2013.01); *A61F 2002/4051* (2013.01); *A61F 2002/4062* (2013.01); *A61F 2002/4631* (2013.01); *A61F 2002/4635* (2013.01); *A61F 2220/0008* (2013.01); *A61F 2220/0033* (2013.01); *A61F 2230/0004* (2013.01); *A61F 2230/0006* (2013.01); *A61F 2230/0008* (2013.01); *A61F 2230/0019* (2013.01); *A61F 2230/0069* (2013.01); *A61F 2250/0097* (2013.01); *A61F 2310/00011* (2013.01); *A61F 2310/00179* (2013.01)

(56) References Cited

U.S. PATENT DOCUMENTS

| | | | |
|---|---|---|---|
| 4,003,095 | A | 1/1977 | Gristina |
| 4,012,796 | A | 3/1977 | Weisman et al. |
| 4,045,826 | A | 9/1977 | Stroot |
| 4,206,517 | A | 6/1980 | Pappas et al. |
| 4,261,062 | A | 4/1981 | Amstutz et al. |
| 4,404,693 | A | 9/1983 | Zweymuller |
| 4,550,450 | A | 11/1985 | Kinnett |
| 4,698,063 | A | 10/1987 | Link et al. |
| 4,700,660 | A | 10/1987 | Levchenko et al. |
| 4,783,192 | A | 1/1988 | Wroblewski et al. |
| 4,827,919 | A | 5/1989 | Barbarito et al. |
| 4,865,605 | A | 9/1989 | Dines et al. |
| 4,908,036 | A | 3/1990 | Link et al. |
| 4,964,865 | A | 10/1990 | Burkhead et al. |
| 4,986,833 | A | 1/1991 | Worland |
| 4,990,161 | A | 2/1991 | Kampner |
| 5,030,219 | A | 7/1991 | Matsen, III et al. |
| 5,032,132 | A | 7/1991 | Matsen, III et al. |
| 5,080,673 | A | 1/1992 | Burkhead et al. |
| 5,108,440 | A | 4/1992 | Grundei |
| 5,282,865 | A | 2/1994 | Dong |
| 5,314,479 | A | 5/1994 | Rockwood, Jr. et al. |
| 5,314,489 | A | 5/1994 | Hoffman et al. |
| 5,344,458 | A | 9/1994 | Bonutti |
| 5,358,525 | A | 10/1994 | Fox et al. |
| 5,370,694 | A | 12/1994 | Davidson |
| 5,437,677 | A | 8/1995 | Shearer et al. |
| 5,462,563 | A | 10/1995 | Shearer et al. |
| 5,480,450 | A | 1/1996 | James et al. |
| 5,489,309 | A | 2/1996 | Lackey et al. |
| 5,489,310 | A | 2/1996 | Mikhail |
| 5,507,748 | A | 4/1996 | Sheehan et al. |
| 5,507,819 | A | 4/1996 | Wolf |
| 5,514,184 | A | 5/1996 | Doi |
| 5,549,683 | A | 8/1996 | Bonutti |
| 5,593,448 | A | 1/1997 | Dong |
| 5,702,447 | A | 12/1997 | Walch et al. |
| 5,702,486 | A | 12/1997 | Craig et al. |
| 5,746,771 | A | 5/1998 | Clement, Jr. et al. |
| 5,755,811 | A | 5/1998 | Tanamal et al. |
| 5,769,856 | A | 6/1998 | Dong et al. |
| 5,800,551 | A | 9/1998 | Williamson et al. |
| 5,928,285 | A | 7/1999 | Bigliani et al. |
| 6,019,766 | A | 2/2000 | Ling et al. |
| 6,037,724 | A | 3/2000 | Buss et al. |
| 6,228,119 | B1 | 5/2001 | Ondria et al. |
| 6,231,913 | B1 | 5/2001 | Schwimmer et al. |
| 6,290,726 | B1 | 9/2001 | Pope et al. |
| 6,334,874 | B1 | 1/2002 | Tornier et al. |
| 6,364,910 | B1 | 4/2002 | Shultz et al. |
| 6,368,353 | B1 | 4/2002 | Arcand |
| 6,379,386 | B1 | 4/2002 | Resch et al. |
| 6,458,136 | B1 | 10/2002 | Allard et al. |
| 6,514,287 | B2 | 2/2003 | Ondria et al. |
| 6,520,964 | B2 * | 2/2003 | Tallarida ............ A61F 2/30756 623/20.14 |
| 6,589,281 | B2 | 7/2003 | Hyde, Jr. |
| 6,610,067 | B2 | 8/2003 | Tallarida et al. |
| 6,620,197 | B2 | 9/2003 | Maroney |
| 6,673,115 | B2 | 1/2004 | Resch et al. |
| 6,679,916 | B1 | 1/2004 | Frankle et al. |
| 6,679,917 | B2 | 1/2004 | Ek |
| 6,699,289 | B2 | 3/2004 | Iannotti et al. |
| 6,709,463 | B1 | 3/2004 | Pope et al. |
| 6,712,823 | B2 | 3/2004 | Grusin et al. |
| 6,761,740 | B2 | 7/2004 | Tornier |
| 6,783,549 | B1 | 8/2004 | Stone et al. |
| 6,875,234 | B2 | 4/2005 | Lipman et al. |
| 6,953,478 | B2 | 10/2005 | Bouttens et al. |
| 7,011,686 | B2 | 3/2006 | Ball et al. |
| 7,044,973 | B2 | 5/2006 | Rockwood et al. |
| 7,238,089 | B2 | 7/2007 | Tsumuraya et al. |
| 7,238,208 | B2 | 7/2007 | Camino et al. |
| 7,261,741 | B2 | 8/2007 | Weisman et al. |
| 7,294,149 | B2 | 11/2007 | Hozack et al. |
| 7,320,709 | B2 | 1/2008 | Felt et al. |
| 7,329,284 | B2 | 2/2008 | Maroney et al. |
| 7,465,319 | B2 | 12/2008 | Tornier |
| 7,517,364 | B2 | 4/2009 | Long et al. |
| 7,618,462 | B2 | 11/2009 | Ek |
| 7,678,151 | B2 | 3/2010 | Ek |
| 7,749,278 | B2 | 7/2010 | Frederick et al. |
| 7,766,969 | B2 | 8/2010 | Justin et al. |
| 7,776,098 | B2 | 8/2010 | Murphy |
| 7,892,287 | B2 | 2/2011 | Deffenbaugh |
| 7,922,769 | B2 | 4/2011 | Deffenbaugh et al. |
| 8,007,538 | B2 | 8/2011 | Gunther |
| 8,038,719 | B2 | 10/2011 | Gunther |
| 8,048,161 | B2 | 11/2011 | Guederian et al. |
| 8,048,167 | B2 | 11/2011 | Dietz et al. |
| 8,303,665 | B2 | 11/2012 | Tornier et al. |
| 8,529,629 | B2 | 9/2013 | Angibaud et al. |
| 8,608,805 | B2 | 12/2013 | Forrer et al. |
| 8,721,726 | B2 * | 5/2014 | Capon ................ A61F 2/4081 623/19.11 |
| 8,778,028 | B2 | 7/2014 | Gunther et al. |
| 8,840,671 | B2 | 9/2014 | Ambacher |
| 8,920,508 | B2 | 12/2014 | Iannotti et al. |

(56) References Cited

U.S. PATENT DOCUMENTS

| | | |
|---|---|---|
| 8,940,054 B2 | 1/2015 | Wiley et al. |
| 9,114,017 B2 | 8/2015 | Lappin |
| 9,283,083 B2 | 3/2016 | Winslow et al. |
| 9,381,086 B2 | 7/2016 | Ries et al. |
| 9,545,311 B2 | 1/2017 | Courtney, Jr. et al. |
| 9,545,312 B2 | 1/2017 | Tornier et al. |
| 9,610,166 B2 | 4/2017 | Gunther et al. |
| 9,615,839 B2 | 4/2017 | Olson |
| 9,693,784 B2 | 7/2017 | Gunther |
| 9,867,710 B2 | 1/2018 | Dalla Pria et al. |
| 10,034,753 B2 | 7/2018 | Dressler et al. |
| 10,143,559 B2 | 12/2018 | Ries et al. |
| 10,357,373 B2 | 7/2019 | Gargac et al. |
| 10,492,926 B1 | 12/2019 | Gunther |
| 10,702,390 B2 | 7/2020 | Chavarria et al. |
| 10,722,373 B2 | 7/2020 | Hodorek et al. |
| 10,779,952 B2 | 9/2020 | Gunther et al. |
| 10,786,265 B2 | 9/2020 | Gunther |
| 10,925,745 B2 | 2/2021 | Cardon et al. |
| 10,966,788 B2 | 4/2021 | Britton et al. |
| 11,065,125 B2 | 7/2021 | Ball |
| 11,166,733 B2 | 11/2021 | Neichel et al. |
| 11,464,645 B2 | 10/2022 | Cardon et al. |
| 11,564,802 B2 | 1/2023 | Ball et al. |
| D977,643 S | 2/2023 | Ball et al. |
| 11,696,772 B2 | 7/2023 | Gunther |
| 2001/0011192 A1 | 8/2001 | Ondria et al. |
| 2001/0037153 A1 | 11/2001 | Rockwood, Jr. et al. |
| 2001/0047210 A1 | 11/2001 | Wolf |
| 2002/0055783 A1 | 5/2002 | Tallarida et al. |
| 2002/0082702 A1 | 6/2002 | Resch et al. |
| 2002/0087213 A1 | 7/2002 | Bertram, III |
| 2002/0095214 A1 | 7/2002 | Hyde, Jr. |
| 2002/0111689 A1 | 8/2002 | Hyde, Jr. et al. |
| 2002/0138148 A1 | 9/2002 | Hyde, Jr. et al. |
| 2003/0100952 A1 | 5/2003 | Rockwood, Jr. et al. |
| 2003/0114933 A1 | 6/2003 | Bouttens et al. |
| 2003/0125809 A1* | 7/2003 | Iannotti ............. A61B 17/1684 623/19.13 |
| 2003/0144738 A1 | 7/2003 | Rogalski |
| 2003/0158605 A1 | 8/2003 | Tournier |
| 2003/0163202 A1 | 8/2003 | Lakin |
| 2003/0236572 A1 | 12/2003 | Bertram, III |
| 2004/0002766 A1 | 1/2004 | Hunter et al. |
| 2004/0039449 A1 | 2/2004 | Tournier |
| 2004/0039451 A1 | 2/2004 | Southworth |
| 2004/0059424 A1 | 3/2004 | Guederian et al. |
| 2004/0064187 A1 | 4/2004 | Ball et al. |
| 2004/0064189 A1 | 4/2004 | Maroney et al. |
| 2004/0064190 A1 | 4/2004 | Ball et al. |
| 2004/0107002 A1 | 6/2004 | Katsuya |
| 2004/0122519 A1 | 6/2004 | Wiley et al. |
| 2004/0122520 A1 | 6/2004 | Lipman et al. |
| 2004/0167629 A1 | 8/2004 | Geremakis et al. |
| 2004/0167630 A1 | 8/2004 | Rolston |
| 2004/0193168 A1 | 9/2004 | Long et al. |
| 2004/0193275 A1 | 9/2004 | Long et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0199260 A1 | 10/2004 | Pope et al. |
| 2004/0220674 A1 | 11/2004 | Pria |
| 2004/0230311 A1 | 11/2004 | Cyprien et al. |
| 2004/0260398 A1 | 12/2004 | Kelman |
| 2005/0043805 A1 | 2/2005 | Chudik |
| 2005/0049709 A1 | 3/2005 | Tornier |
| 2005/0065612 A1 | 3/2005 | Winslow |
| 2005/0107882 A1 | 5/2005 | Stone et al. |
| 2005/0119531 A1 | 6/2005 | Sharratt |
| 2005/0177241 A1 | 8/2005 | Angibaud et al. |
| 2005/0261775 A1 | 11/2005 | Baum et al. |
| 2005/0278030 A1 | 12/2005 | Tornier et al. |
| 2006/0036328 A1 | 2/2006 | Parrott et al. |
| 2006/0069443 A1 | 3/2006 | Deffenbaugh et al. |
| 2006/0069444 A1 | 3/2006 | Deffenbaugh et al. |
| 2006/0069445 A1 | 3/2006 | Ondrla et al. |
| 2006/0200249 A1 | 9/2006 | Beguin et al. |
| 2007/0038302 A1 | 2/2007 | Shultz et al. |
| 2007/0050042 A1 | 3/2007 | Dietz et al. |
| 2007/0055380 A1 | 3/2007 | Berelsman et al. |
| 2007/0112433 A1 | 5/2007 | Frederick et al. |
| 2007/0156246 A1 | 7/2007 | Meswania et al. |
| 2007/0179624 A1 | 8/2007 | Stone et al. |
| 2007/0225817 A1 | 9/2007 | Ruebelt et al. |
| 2007/0225818 A1 | 9/2007 | Reubelt et al. |
| 2008/0021564 A1 | 1/2008 | Gunther |
| 2008/0082175 A1 | 4/2008 | Holovacs et al. |
| 2008/0177327 A1 | 7/2008 | Malandain et al. |
| 2008/0234820 A1 | 9/2008 | Felt et al. |
| 2008/0294268 A1 | 11/2008 | Baum et al. |
| 2009/0105837 A1 | 4/2009 | LaFosse et al. |
| 2009/0125113 A1 | 5/2009 | Guederian et al. |
| 2009/0228112 A1 | 9/2009 | Clark et al. |
| 2009/0287309 A1 | 11/2009 | Walch et al. |
| 2010/0087876 A1 | 4/2010 | Gunther |
| 2010/0087877 A1 | 4/2010 | Gunther |
| 2010/0114326 A1 | 5/2010 | Winslow et al. |
| 2010/0161066 A1 | 6/2010 | Ionetti et al. |
| 2010/0217399 A1 | 8/2010 | Groh |
| 2010/0274360 A1 | 10/2010 | Gunther |
| 2011/0029089 A1 | 2/2011 | Giuliani et al. |
| 2011/0106266 A1 | 5/2011 | Schwyzer et al. |
| 2011/0137424 A1 | 6/2011 | Lappin et al. |
| 2011/0144758 A1 | 6/2011 | Deffenbaugh |
| 2011/0276144 A1 | 11/2011 | Wirth et al. |
| 2011/0313533 A1 | 12/2011 | Gunther |
| 2012/0209392 A1 | 8/2012 | Angibuad et al. |
| 2012/0239156 A1 | 9/2012 | De Wilde et al. |
| 2013/0060346 A1 | 3/2013 | Collins |
| 2013/0090736 A1 | 4/2013 | Katrana et al. |
| 2013/0150972 A1 | 6/2013 | Iannotti et al. |
| 2013/0150974 A1 | 6/2013 | Iannotti et al. |
| 2013/0194353 A1 | 8/2013 | Hirai et al. |
| 2013/0197651 A1 | 8/2013 | McDaniel et al. |
| 2014/0025173 A1 | 1/2014 | Cardon et al. |
| 2014/0107794 A1 | 4/2014 | Deffenbaugh et al. |
| 2014/0253641 A1 | 9/2014 | Furuya |
| 2014/0257499 A1 | 9/2014 | Winslow et al. |
| 2015/0223941 A1 | 8/2015 | Lang |
| 2015/0265411 A1 | 9/2015 | Deransart et al. |
| 2016/0045323 A1 | 2/2016 | Kovacs et al. |
| 2016/0302934 A1 | 10/2016 | Chavarria et al. |
| 2017/0056187 A1 | 3/2017 | Humphrey et al. |
| 2017/0071749 A1 | 3/2017 | Lappin et al. |
| 2017/0209275 A1 | 7/2017 | Levy |
| 2017/0273806 A1 | 9/2017 | Cardon et al. |
| 2017/0304063 A1 | 10/2017 | Hatzidakis et al. |
| 2018/0071104 A1 | 3/2018 | Kovacs et al. |
| 2018/0078377 A1 | 3/2018 | Gargac et al. |
| 2018/0161169 A1 | 6/2018 | Cardon et al. |
| 2018/0193150 A1 | 7/2018 | Winslow et al. |
| 2018/0200067 A1 | 7/2018 | Axelso, Jr. et al. |
| 2018/0333268 A1 | 11/2018 | Cardon et al. |
| 2019/0336293 A1 | 11/2019 | Kehres |
| 2020/0261209 A1 | 8/2020 | Stchur et al. |
| 2020/0315808 A1 | 10/2020 | Goldberg et al. |
| 2021/0038401 A1 | 2/2021 | Ball et al. |
| 2021/0137692 A1 | 5/2021 | Budge |
| 2021/0137693 A1 | 5/2021 | Ball et al. |
| 2021/0236292 A1 | 8/2021 | Chavarria et al. |
| 2021/0244547 A1 | 8/2021 | Gunther et al. |
| 2021/0251640 A1 | 8/2021 | Gunther |
| 2021/0338446 A1 | 11/2021 | Ball |
| 2022/0151795 A1 | 5/2022 | Running et al. |
| 2022/0175543 A1 | 6/2022 | Ball |
| 2022/0175544 A1 | 6/2022 | Ball et al. |
| 2023/0080207 A1 | 3/2023 | Gunther et al. |

FOREIGN PATENT DOCUMENTS

| | | |
|---|---|---|
| EP | 0299889 A2 | 1/1989 |
| EP | 0339530 A2 | 11/1989 |
| EP | 0570816 A1 | 11/1993 |
| EP | 1464305 A1 | 10/2004 |

(56) References Cited

FOREIGN PATENT DOCUMENTS

| | | |
|---|---|---|
| EP | 1858453 | 11/2007 |
| EP | 1952788 A1 | 8/2008 |
| EP | 2601912 | 6/2013 |
| EP | 2083759 B1 | 9/2015 |
| EP | 3090705 | 11/2016 |
| EP | 3598957 | 7/2018 |
| FR | 2248820 A1 | 5/1975 |
| FR | 2567019 A1 | 1/1986 |
| FR | 2695313 A1 | 3/1994 |
| JP | 2013-158909 | 8/2013 |
| JP | 2014-515651 | 7/2014 |
| WO | WO 2006/093763 | 8/2006 |
| WO | WO 2008/011078 A2 | 1/2008 |
| WO | WO 2009/071940 A1 | 6/2009 |
| WO | WO 2011/112425 | 9/2011 |
| WO | WO 2013/148437 | 10/2013 |
| WO | WO 2012/075183 | 4/2014 |
| WO | WO 2014/067961 | 5/2014 |
| WO | WO 2014/0195909 | 12/2014 |
| WO | WO 2017/184792 | 10/2017 |
| WO | WO 2018/022227 | 2/2018 |
| WO | WO 2018/129286 | 7/2018 |
| WO | WO 2018/181420 | 10/2018 |
| WO | WO 2019/006205 | 1/2019 |
| WO | WO 2019/178104 | 9/2019 |
| WO | WO 2019/213073 | 11/2019 |
| WO | WO 2020/023975 | 1/2020 |
| WO | WO 2020/185893 | 9/2020 |

OTHER PUBLICATIONS

U.S. Appl. No. 16/701,118, filed Dec. 2, 2019, Gunther.
U.S. Appl. No. 29/870,666, filed Feb. 1, 2023, Ball et al.
U.S. Appl. No. 18/349,805, filed Jul. 10, 2023, Gunther.
Biomet, "Absolute™ Bi-Polar." 2001 in 2 pages.
Biomet, "Copeland"™ Humeral Resurfacing Head, Interlok®/HA Coated Implant Information, 2003 in 1 page.
Biomet, "Copeland"™ Humeral Resurfacing Head, 2001 in 12 pages.
Biomet, "Copeland™ Humeral Resurfacing Head, Macrobond™ Implant Information," 2003 in 1 page.
Biomet, "Copeland™ Humeral Resurfacing Head, Surgical Technique," 2003 in 2 pages.
Boileau et al., "The Three-Dimensional Geometry of the Proximal Humerus. Implications for Surgical Technique and Prosthetic Design," J. Bone Joint Surg. Br. 79: 857-865, 1997.
Braun, et al., Modular Short-stem Prosthesis in Total Hip Arthroplasty: Implant Positioning and the Influence of Navigation, Ortho SuperSite (Oct. 2007) in 8 pages.
Clavert et al. Glenoid resurfacing: what are the limits to asymmetric reaming for posterior erosion? J. Shoulder and Elbow Surg. Nov./Dec. 2007: 843-848.
Dalla Pria, Paolo. Slide presentation, entitled "Shoulder Prosthesis Design and Evolution", to the Naples International Shoulder Congress in Italy (2000) in 55 pages.
Depuy, "Global C.A.P., Surgical Technique Resurfacing Humeral Head Implant," 2004 in 23 pages.
Inset Mini-glenoid Brochure, Titan Modular Shoulder System Brochure, Ascension Orthopedics, 2011, 4 pages.
Karduna et al. Glenhumeral Joint Translations before and after Total Shoulder Arthroplasty. J. Bone and Joint Surg. 79(8) (1997): 1166-1174.
Redacted letter from a third party dated Aug. 24, 2012 in 2 pages.
Levy et al., "Cementless Surface Replacement Arthroplasty of the Should. 5- to 10-year Results with the Copeland Mark-2 Prosthesis," J. Bone Joint Surg. Br. 83: 213-221, 2001.
Lima-Lto Medical Systems Glenoidi/Glenoids catalogue (2001) in 1 page.
Lima-Lto Miniglenoide Cementata document 7560.50.030 (1999) in 1 page.
Panisello, et al., Bone remodelling after total hip arthroplasty using an uncemented anatomic femoral stem: a three-year prospective study using bone densitometry, J Ortho Surg 14(1):32-37 (2006).
Ross, Mark and Duke, Phillip, "Early Experience In The Use of a New Glenoid Resurfacing Technique" Glenoid Presentation, SESA Nov. 4, 2006, Session 4/0800-0930 p. 93 in 1 page.
Invitation to Pay Additional Fees in PCT/US2023/015740, dated May 24, 2023.
International Search Report and Written Opinion in PCT/US2023/015740, dated Jul. 17, 2023.
Tight Fit Tools, Right Angle Drill Attachment, Serial No. 00400 www.tightfittools.com/riganat.html in 1 page/downloaded Mar. 11, 2005.
Titan(™) Modular Shoulder System Brochure, 2011, available at http://www.ascensionortho.com/Assets/PDF/TitanModular/TITANModularShoulder_Brochure-revD.pdf (2 pages).
Tournier et al., Enhancement of Glenoid Prosthesis Anchorage using Burying Technique. Techniques in Shoulder & Elbow Surgery 9(1)(2008): 35-42.
Wang et al., Biomechanical Evaluation of a Novel Glenoid Design in Total Shoulder Arthroplasty. J. Shoulder & Elbow Surgery (2005) 15: 129S-140S.
Statement of Grounds and Particulars of Opposition for Australian Patent Application No. 2006218936 dated Oct. 5, 2012 in 8 pages.

\* cited by examiner

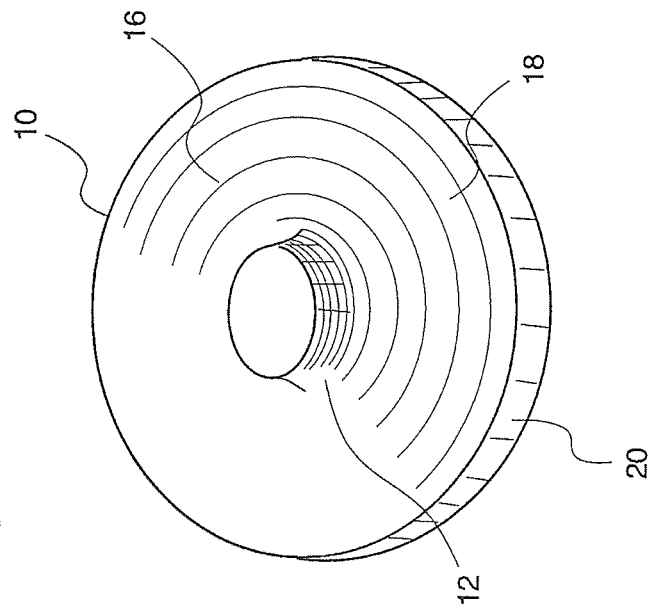
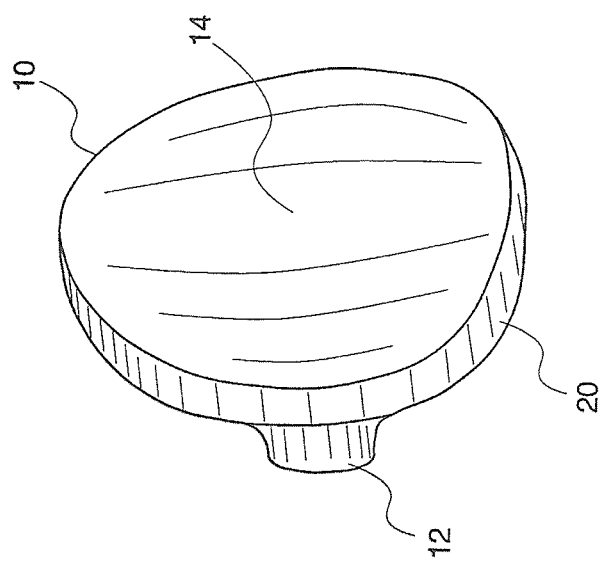

METHODS AND DEVICES FOR LESS INVASIVE GLENOID REPLACEMENT

CROSS-REFERENCE TO RELATED APPLICATIONS

This is a continuation of U.S. application Ser. No. 17/027,493, filed Sep. 21, 2020, which is a continuation of U.S. application Ser. No. 15/477,316, filed Apr. 3, 2017, now U.S. Pat. No. 10,779,952, which is a continuation of U.S. application Ser. No. 14/329,853, filed Jul. 11, 2014, now U.S. Pat. No. 9,610,166, which is a continuation of U.S. application Ser. No. 12/719,182, filed Mar. 8, 2010, now U.S. Pat. No. 8,778,028, which is a continuation-in-part of U.S. application Ser. No. 11/066,978, filed Feb. 25, 2005, now U.S. Pat. No. 8,007,538. The entireties of these applications are all hereby incorporated by reference herein and made a part of the present specification.

FIELD OF THE INVENTION

The present invention relates to the field of glenoid surface replacement.

BACKGROUND OF THE INVENTION

The invention provides a glenoid shoulder implant, a humeral implant, and devices for preparing the glenoid and humeral head for joint replacement.

Shoulder replacement surgery is currently used to treat patients suffering from disabling pain due to worn or damaged shoulder joints, which can be caused by, e.g., arthritis or injury. The humeral implants currently in use are typically made from metal, and the implants are affixed to the bone using bone cement (e.g., polymethylmethacrylate) or by press fitting the implant into the bone using a roughened outer surface coating on the metal for bony integration. Most glenoid (shoulder socket) implants are made completely from polyethylene and affixed to the cortical bone using bone cement. Some glenoid implants have a rigid base plate made of metal, ceramic or rigid polymer with a polyethylene insert. The polyethylene material is suitable as a low friction articulating surface for engaging the humeral component. Current glenoid implants are intended to sit on a prepared surface of a glenoid bone. The surface is typically prepared by removing any remaining cartilage, reaming a smooth bony surface and by drilling receiving pockets for anchoring features or devices within the natural glenoid area. Current implant designs use either a keel or multiple elongated pegs on the back (medial surface) of the prosthetic glenoid implant as anchoring features to secure the glenoid implant inside the glenoid vault.

Glenoid implants with keeled or elongated peg anchors suffer from several disadvantages, which limit their lifespan once implanted and reduce the number of indications for which they can be used. For example, these glenoid implants can loosen due to poor fixation to the bone, and are prone to wear and fatigue failure of the polyethylene due to adhesion, abrasion, and shear stress. Because of these deficiencies, surgeons hesitate to perform glenoid replacement surgery on young or middle aged patients with glenoid articular cartilage injuries or damage due to early arthritis for fear that the implant may not last more than 10-15 years in the body, thus subjecting the patient to the possibility of two or more surgeries during the lifetime of the patient to preserve the function and pain-free state of the joint. Finally, current glenoid implants with a long keel or an elongated anchor peg are sometimes contraindicated in patients with significant glenoid bone loss. As arthritis progresses, the humeral head can wear medially and destroy the foundation of glenoid bone. In these cases, the glenoid vault can be significantly reduced in volume and depth. Thus, a typical keel or peg design can penetrate through the glenoid vault and injure the suprascapular nerve along the suprascapular notch or spinoglenoid notch with resultant denervation injury to the rotator cuff muscles. Penetrating through the bone of the glenoid vault can also fracture the body of the scapula and cause early implant loosening.

There are also several disadvantages associated with current glenoid replacement surgical techniques. Current techniques require extensive shoulder exposure with capsular releases in order to fully expose the glenoid surface circumferentially. Since the axillary nerve is located within 1 cm of the inferior capsule, there is potential risk of axillary nerve injury with resultant denervation injury to the deltoid muscle when these releases are performed. Use of the current glenoid implants with keels or elongated anchor pegs requires this extensive glenoid exposure for proper fitting and placement of the prostheses. Current glenoid replacement surgery also requires a long skin incision, typically 150 mm to 200 mm in length, and extensive soft tissue stripping in order to fully expose the glenoid circumferentially, which increases the risk of tissue damage and produces a cosmetically unappealing scar. Finally, current glenoid replacement surgical techniques require advanced surgical training and expertise within the specialty of shoulder surgery, yet the majority of shoulder implants performed in the U.S. every year are performed by orthopedic surgeons who do not have advanced training in the subspecialty of shoulder surgery. Therefore, many surgeons have difficulty preparing the glenoid site for a total shoulder replacement using the current techniques.

As a consequence of the limitations of the currently available designs and surgical techniques some patients forego surgery and incur a risk of continued pain and disability. Patients who elect a surgical solution incur the risk of neurovascular injuries, glenoid and scapula fractures, and failed shoulder prostheses requiring revision surgery. Thus, there remains a need for an improved glenoid implant and improved methods for performing replacement shoulder surgery.

SUMMARY OF THE INVENTION

There is provided in accordance with one aspect of the present invention, a method of treating a patient. The method comprises the steps of identifying a patient having a glenoid surface, and reaming a cavity into the glenoid surface. A glenoid implant is inserted into the cavity, such that at least a portion of a peripheral edge of the implant resides below the adjacent glenoid surface, and the portion residing below the adjacent glenoid surface is circumferentially surrounded by the cortical bone of the glenoid.

The reaming a cavity step comprises reaming a circular cavity so as to create a mating surface for the prosthetic glenoid implant, said surface being below the native glenoid bone surface and being circumferentially surrounded by native glenoid bone. The inserting a glenoid implant step may comprise fitting a glenoid implant having a circular portion into the cavity, said circular portion having a diameter complimentary to that of the cavity reamed in the glenoid bone The method may additionally comprise the step of securing the implant within the cavity using bone cement or mechanical engagement such as can be achieved using a press-fit interference or bone screws. The implant has a medial surface disposed to engage the prepared surface within the reamed cavity. Various configurations of this medial surface are presented, these surface geometries being configured to receive bone cement and improve adhesion of the implant to, and retention within, the reamed bone cavity.

The method may additionally comprise the step of stabilizing the implant within the cavity using a central peg extending from a medial surface of the implant, said peg being located within a prepared receiving hole in the glenoid bone Various geometric configurations of this peg are presented.

The method may additionally comprise the step of accessing the glenoid via a deltopectoral approach. Alternatively, the method may comprise the step of accessing the glenoid via an anterolateral approach.

In certain implementations of the invention, the reaming a cavity step comprises reaming a cavity completely within the boundary of the native glenoid cavity, without destroying the peripheral margin of the glenoid surface. This step may be accomplished while leaving the majority of the inferior capsule intact. The reaming a cavity step may comprise reaming a cavity while leaving the peripheral cortex intact. The method may include the step of accessing the glenoid surface via an incision having a length of no more than about 9 cm.

In the patients having more extensive deficiency of glenoid bone there is often a need to reconstruct the natural geometry of the shoulder so as to restore the natural orientation and engagement of the humerus to glenoid interface. This is often currently achieved by grafting bone tissue or otherwise reconstructing the bony geometry of the glenoid structure. In one aspect of the glenoid prosthesis invention disclosed herein there is a circular prosthesis configuration presented whereon the plane of the articulating surface is offset from the plane of the medial, bone engaging, surface of the implant. The combination of a circular implant and included angles between the medial and articulating surfaces of the implant device allows for in-situ positioning of the implant by rotating the circular implant around the central axis of the medial surface in order to restore the natural plane of the glenoid value.

In certain patients there is extreme bone deficiency or there exists an atypical bone wear pattern, in these case there may remain insufficient bone in which to create a reamed cavity which completely surrounds the perimeter of the glenoid implant. In one implementation the invented glenoid implant device has an annular ring disposed around the circumference of the medial surface. During the cavity reaming step of the surgical procedure a perimeter groove is cut into the glenoid bone structure around the circumference of the reamed cavity so as to create a receiving channel around the perimeter of the reamed cavity in the bone, this groove receives within it a corresponding annular ring of the glenoid implant device thereby creating full circumferential engagement of the implant within the bone in order to increase the retention and stability of said implant.

There is further presented a geometry for the articulating surface of the device which permits a semi-constrained relationship between the glenoid implant device and the humeral head.

In accordance with a further aspect of the present invention, there is provided a glenoid implant. The implant comprises a circular body, having a medial surface, an articulating surface, a peripheral edge and central axis. A post is provided on the medial surface, disposed concentrically on the central axis. At least one axially extending flange extends from the medial surface at the peripheral edge of the circular body.

Preferably, the at least one flange extends around at least about 75% of the peripheral edge of the circular body. The flange may extend at least about 85% or 95% of the way around the peripheral edge of the circular body, and may be discontinuous or continuous.

The circular body has a first thickness measured in the axial direction at a first point on the peripheral edge, and a second thickness measured in the axial direction at a second point on the peripheral edge which is spaced apart from the first point by 180°. In one implementation of the invention, the first thickness is substantially equal to the second thickness. Alternatively, the first thickness may be at least about 125% of the of the second thickness, at least about 150% of the second thickness, or at least about 200% of the second thickness to provide an angled, rotationally adjustable implant.

In accordance with a further aspect of the present invention, there is provided a glenoid implant. The implant comprises a circular body, having a medial surface, an articulating surface, a peripheral edge and a central axis. A post is provided on the medial surface, disposed concentrically on the central axis. The body comprises a first thickness measured in the axial direction at a first point on the peripheral edge, and a second thickness measured in the axial direction at a second point on the peripheral edge, spaced apart from the first point by 180°. The first thickness is at least about 125% of the second thickness. The implant may additionally comprise at least one projection extending axially from the body at the peripheral edge. The projection may comprise an annular flange, which may be continuous or discontinuous. The implant may additionally comprise at least one bone cement flow channel on the medial surface.

In accordance with a further aspect of the present invention, there is provided a method of treating a patient. The method comprises the steps of exposing a glenoid surface, and reaming a circular depression in the glenoid surface. A glenoid implant is provided, having a circular peripheral edge and a non-spherical concavity with an articulating surface, the concavity having an axis of rotation which is angularly offset from an axis of the circular peripheral edge. The implant is positioned such that the circular peripheral edge at least partially resides within the circular depression. The implant is thereafter rotated, to direct the axis of rotation of the articulating surface to a desired position.

In accordance with a further aspect of the present invention, there is provided a method of treating a patient. The method comprises the steps of making a skin incision, and exposing a glenoid surface through the incision. A reamer is introduced through the incision, and a circular depression is reamed within the glenoid surface. The glenoid implant is introduced through the incision, and positioned at least partially within the depression. The incision is preferably no more than about 100 mm in length.

In accordance with a further aspect of the present invention, there is provided a cement construct, for retaining an implant within a cavity in a bone. The construct comprises a cement shell, having a concave side corresponding to the configuration of an implant and a convex side corresponding to the configuration of a prepared cavity in a bone. The concave side has an axis of rotational symmetry. A first tubular wall section is concentrically disposed about the axis, and a substantially planar section extends radially outwardly from an end of the first tubular wall section and transverse to the axis.

A second tubular wall section is concentrically disposed about the axis, and extends axially from a peripheral edge of the planar section. The second tubular wall section extends at least about 180°, preferably at least about 270°, and in certain implementations completely around the axis.

In accordance with another aspect of the present invention, there is provided a method of preparing a glenoid surface for implantation of a glenoid implant. The method comprises the steps of reaming a circular depression in the glenoid surface, to produce a reduced glenoid surface having an axis of rotation. A bore is reamed coincident with the axis, and below the level of the reduced surface. An annular channel is reamed concentrically about the axis, and below the level of the reduced surface.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 2A is an anterior surface view of the circular glenoid implant of the invention that includes a single short backside peg.

FIG. 2B is a backside view of the circular glenoid implant of FIG. 2B.

FIG. 33 further illustrates the reamed cavity having an annular recess at the circumference to receive a corresponding protruding feature of a prosthetic glenoid device.

DETAILED DESCRIPTION OF THE PREFERRED EMBODIMENT

Figure 1C:
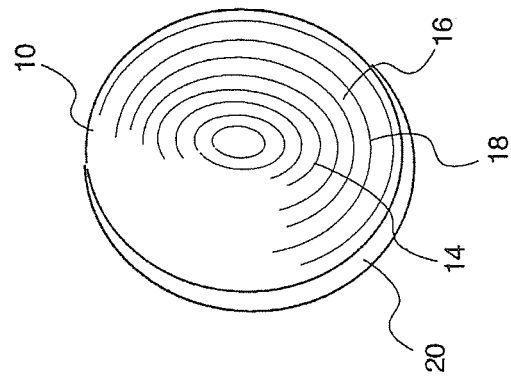
FIG. 1C is a backside view of the circular glenoid implant of FIG. 1A

The invention features an inset glenoid implant prosthesis, a humeral implant prosthesis, and methods and devices for preparing the surgical site for implantation of the implant prostheses.

In one aspect, the invention features an inset glenoid shoulder implant that is implanted within the glenoid vault, thereby allowing circumferential cortical support along the rim of the prosthesis, which improves fixation strength in comparison to current glenoid implants. Another advantage of the glenoid implant is that it requires only a minimal amount of bone removal for implantation.

The glenoid implant itself includes a (1) body portion having (i) a smooth concave lateral articulating surface facing away from the scapula, which is adapted to be engaged by a convex surface of a humeral component, and (ii) an opposing surface on the medial side intended to be positioned within a cavity reamed in the glenoid. In a preferred embodiment, the glenoid implant also includes (2) a short peg on the medial side extending centrally outward along an axis from a convex or flat backside (medial) surface of the glenoid implant. In a preferred embodiment, the short peg of the glenoid implant is less than about 10 mm long, more preferably about 8 mm or less in length, even more preferably about 5 mm or less in length. Alternatively, the glenoid implant has multiple pegs, each of which can be the same length or different lengths, e.g., less than about 8 mm or less in length, more preferably about 5 mm or less in length. In another embodiment, at least one of the pegs is between about 5 mm and about 8 mm in length and the remaining pegs are less than about 8 mm in length.

In another preferred embodiment, the body portion extends to an edge having a circular configuration while, in a second embodiment, the body portion has an edge defining a non-circular configuration, such as an oval, an elongated configuration, or a configuration which may be characterized as rectangular with slightly rounded ends. In another preferred embodiment, the glenoid implant is implanted in a prepared cavity of the glenoid which conforms generally to the backside (medial) surface only and sits inset slightly within the glenoid vault. In another preferred embodiment, the glenoid implant is implanted in a prepared cavity of the glenoid which conforms generally to the single short peg or multiple short pegs, if present, and the backside (medial) surface of the glenoid implant.

In another preferred embodiment, the glenoid implant of the invention is manufactured using polyethylene, metal, or ceramic, or combinations thereof, e.g., a combination of metal and polyethylene or ceramic and polyethylene.

In another preferred embodiment, the glenoid implant of the invention is secured to the glenoid using cement fixation or press fit technique. In yet another preferred embodiment, the glenoid implant is further secured to the glenoid using screws, e.g., in press fit designs.

In another preferred embodiment, the glenoid implant can be customized during the surgical procedure, as is required based on the condition of the patient. In another embodiment, the glenoid implant is sterilized prior to implantation. In yet another embodiment, the glenoid implant is provided in sterile packaging.

In the method of implanting the glenoid component, the first step after exposing the glenoid cavity is to determine the appropriate size of component to be used. This is done by placing a series of circular sizers having varying diameters over the glenoid cavity to determine the proper diameter to which the scapula should be reamed at the surface defining the glenoid cavity and the proper size of glenoid component. Using a combined sizer/guide having a central hole and passageway formed therein to determine the correct location and attitude, a hole is drilled a few millimeters into the scapula through the glenoid surface using a combined guide wire/drill. The guide wire/drill is calibrated in order to readily determine the depth of drilling and is attached to a chuck if a power drill is used or a T-handle or the like if the drilling is manual. The guide wire/drill should be drilled into the scapula substantially perpendicular to the anatomic axis of the glenoid surface. Thereafter, the combined sizer/guide is removed and a reamer is positioned to ream the scapula to the proper shape and depth forming a cavity having a circular cross-sectional configuration for a circular implant or an oval configuration for an oval implant in a plane normal to the axis defined by the guide wire.

In another aspect of the invention, the glenoid implant can be used in patients with deficient glenoid bone due to fracture or severe arthritis. In preferred embodiments, the glenoid implant has none, one, two, or three or more short backside pegs that do not extend beyond about 10 mm outwardly from the backside (medial) surface of the glenoid implant. In a preferred embodiment, the peg or pegs do not extend beyond about 8 mm from the backside (medial) surface of the glenoid implant. Because the glenoid implant lacks a long backside extension, it can be safely placed inside a glenoid vault with minimal depth. This minimizes the risk of fracturing the body of the scapula or injuring the suprascapular nerve or rotator cuff.

Another aspect of the invention features a humeral implant for use in a total shoulder replacement procedure. The humeral implant of the present invention is less than 70 mm in length, preferably about 60 mm in length, and is less than 40 mm wide anterior to posterior (preferably 20 to 30 mm wide). In an embodiment, the humeral implant includes a collar, which prevents the humeral implant from embedding too deeply in the humerus. In other embodiment, the humeral implant includes a flange (fin), which provides fixation of the humeral implant in the medial to lateral plane and rotational control. Alternatively, the humeral implant can contain 3 flanges (fins) with 1 lateral, 1 anterior, and 1 posterior. The stem of the humeral implant defines a longitudinal axis and the planar surface extends from between about 45° to about 60° to the axis of the stem. The proximal end of the stem includes a bore that extends downward from the planar surface and is adapted to be engaged by an artificial humeral head by means of a morse taper. In other embodiments, the humeral implant is fixed using a bone cement, such as polymethylmethacrylate (PMMA) or a compatible fixation material, or it is press-fit without bone cement. The humeral implant can be customized during the surgical procedure, as is required based on the condition of the patient. In another embodiment, the humeral implant is sterilized prior to implantation. In another embodiment, the humeral implant is provided in sterile packaging. In another preferred embodiment, the humeral implant of the invention is manufactured using polyethylene, metal, or ceramic, or combinations thereof, e.g., a combination of metal and polyethylene or ceramic and polyethylene.

Another aspect of the invention features a cutting jig for preparing a humerus for replacement by a humeral implant. The humeral head cutting jig is a simple, low profile humeral cutting jig that can be a fill circle or part thereof. The cutting jig is placed along the anatomic neck of the humerus in the appropriate version (angle of the cut) as determined by the surgeon. The cutting jig can be secured along the anatomic neck of the proximal humerus using K-wires, pins, or screws and is removed after completion of humeral head resection. In an embodiment, the cutting jig includes a handle portion.

Another aspect of the invention features a method for providing a shoulder implant which can be performed through a minimal incision technique ("mini-incision"). Instead of an extensive deltopectoral approach involving extensive soft tissue stripping, capsular releases, and circumferential glenoid exposure, this inset implant can be performed through a more limited mini-incision technique. A mini-deltopectoral incision is utilized. The skin incision is shorter, and the pectoralis tendon is left intact. The majority of the inferior capsule is also left intact. In a preferred embodiment, the glenoid labrum can be left intact if this is preferred by the surgeon. The central portion of the glenoid bone is then reamed while leaving the peripheral cortex intact. There are three major consequences of this mini-incision technique:

1—Shortening the length of the incision and exposure provides a more cosmetic incision for the patient.
2—Avoiding an extensive inferior capule incision increases the safety of the procedure by reducing the risk of injury to the axillary nerve.
3—Providing an implant that can be placed in the glenoid without extensive, circumferential glenoid exposure would allow general orthopedists to perform a shoulder replacement with less difficulty and potentially fewer complications.

The present invention is also directed to a method for implanting such glenoid implant for precise placement in the scapula and precise drilling and reaming of the scapula. The method is performed using a specialized power drill having a lateral drilling attachment and a short drill bit incorporated into the attachment, which is used to drill a central hole in the glenoid surface. The bone is then reamed with a reamer bit attached to the drill. The lateral drilling attachment inclines the axis of the drill relative to the axis of the access pathway by an angle within the range of from about 45° to about 110°, often within the range of from about 50° to about 90°, and, in one implementation about 60°.

Another aspect of the invention features a slim design power drill for preparing a glenoid for implantation of a glenoid implant, in which the power drill includes a right angle drilling attachment having an extension rod with a length of at least 10 cm, more preferably at least 12, 15, or 18 cm long, the end of which is includes a collet or chuck that is positioned at a 90° angle relative to the extension rod and which is adapted to receive a short drill bit; the power drill being prepared for use in the surgical field by sterilization. In a preferred embodiment, the drill and accessories are sterilized and provided in a sterile container. In other preferred embodiments, the drill bit is 10 mm long, more preferably 12, 14, 16, 18, or 20 mm long, and most preferably 25, 35, 45, 55, 65, or 75 mm long. In other preferred embodiments, the drill bit has the following diameters: 1.5 mm, 2.5 mm, 3.0 mm, 3.2 mm, 4.0 mm, 4.5 mm, 5.0 mm, 5.5 mm, 6.0 mm, 6.5 mm, 7.0 mm, 8.0 mm, 9.0 mm, or 10.0 mm. The power drill is designed to allow drilling in spaces as tight as 50 mm. In other preferred embodiments, the overall length of the right angle drilling attachment is 18 cm, more preferably 20 cm, most preferably 22 cm. The head width and extension rod diameter are preferably less than 25 mm, more preferably less than 22 mm, and most preferably less than 20 mm. The head length is preferably less than 30 mm, more preferably less than 28 mm, and most preferably less than 25 mm. In other preferred embodiments, the right angle drilling attachment is designed to be attached to any power drill, the use of which is acceptable in a surgical field, and is designed to be lightweight, e.g., less than about 200 grams, more preferably less than about 180 grams, and most preferably less than about 150 grams. The power drill can be powered using a battery supply (cordless) or it can be powered using an electrical cord powered from a standard electrical outlet. See, e.g., U.S. Pat. No. 6,037,724, incorporated herein by reference.

The design of the glenoid implant of the invention provides increased implant fixation strength to glenoid bone and therefore decreases the rate of glenoid implant loosening. This implant is also designed for use in cases of deficient glenoid bone which would preclude the use of a current glenoid implant since they require adequate bone in the glenoid vault to support multiple long pegs or a keel.

The invention also features a humeral implant, which is less than 70 mm in length, preferably about 60 mm in length, and is less than 40 mm wide from anterior to posterior (preferably 20-30 mm). The humeral implant of the invention is significantly shorter and thinner (in the anterior to posterior dimension) than most current stems, which are about 70-115 mm in length and bulkier in the proximal (metaphyseal) area than distally both in the anterior to posterior dimension and medial to lateral dimension. Because the humeral implant of the invention is shorter, it can be implanted in a narrower metaphyseal area and does not require the removal of a significant amount of bone. Fixation of the present humeral implant depends upon good interference fixation in the medial-lateral plane when press fit (similar to some current total hips). The humeral implant can be fixed using a bone cement, such as polymethylmethacrylate (PMMA) or a compatible fixation material. Alternatively, the humeral implant can be press-fit.

The invention also features a minimal incision shoulder arthroplasty technique that allows replacement of the glenoid surface and humeral head with only a small incision and less extensive soft tissue stripping. The "mini-incision" procedure also leaves the pectoralis tendon and the majority of the inferior capsule intact. The glenoid labrum can also be left intact. The central portion of the glenoid bone is then reamed while leaving the peripheral cortex intact. The advantages of this "mini-incision" procedure include a shorter incision with less scarring, increased safety, and a more simple exposure of the glenoid, thus allowing general orthopedists to perform a shoulder replacement with less difficulty and potentially fewer complications.

The glenoid implant of the invention lacks a keel and multiple long pegs, which are typically present in the prior art glenoid implants. Instead, the glenoid implant of the invention optionally includes one or more pegs or flanges disposed radially symmetrically about a central axis of the implant, such as only a single short (less than about 8 mm), central backside peg which stabilizes the glenoid implant. The glenoid implant of the invention does not require a long extended keel or long pegs because the majority of the fixation strength is concentrated on the rim of the embedded implant. This obviates the need for significant backside fixation. The fixation, with either cement or press fit techniques, offers circumferential cortical bone fixation around the prosthesis. The shear stresses placed on the implant are therefore supported by a circumferential buttress of bone, which is more mechanically sound than an onlay prosthesis with an extended backside keel or multiple long pegs.

An object of the invention is to minimize the common complications of glenoid implant loosening and fatigue failure that exist with current glenoid implants. All previous glenoid implants sit on the surface of a reamed articular surface and utilize a keel or multiple pegs to secure the implant inside the glenoid vault (see, e.g., FIGS. 3-6). This invention features a glenoid implant (which can be polyethylene, metal, ceramic, or combinations thereof) that is not designed to be placed on the surface of the reamed glenoid articular cartilage. Rather, the present implant is designed to be inset partially (e.g. at least about 1 mm or 2 mm or 3 mm or 4 mm or more below the native adjacent surface of the bone at at least one point around the circumference of the implant) or fully within the glenoid vault (see FIG. 7). The implant may be press fit or cemented in the reamed cavity within the glenoid bone.

Patients who can benefit from the use of the glenoid implant of the invention and the improved methods for performing a total shoulder arthroplasty include young, middle, and older patients with arthritis (typical total shoulder replacement (TSR) patients) or damage or injury to the shoulder. This new inset glenoid implant allows TSR surgery for new, previously contraindicated applications, including applications in which the patient presents with bone defects on the glenoid. The glenoid implant of the invention can also be utilized in revision surgeries.

Figure 1B:
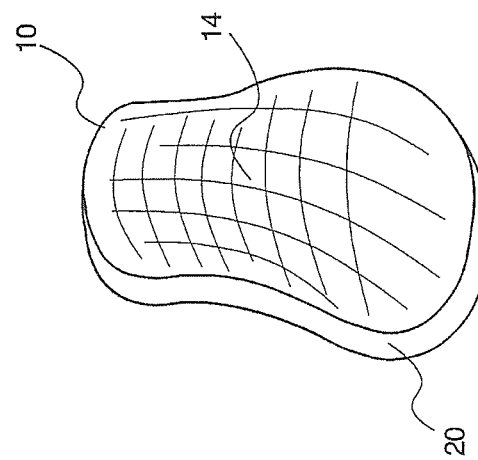
FIG. 1B is an anterior surface view of the oval glenoid implant of the invention.
Figure 1A:
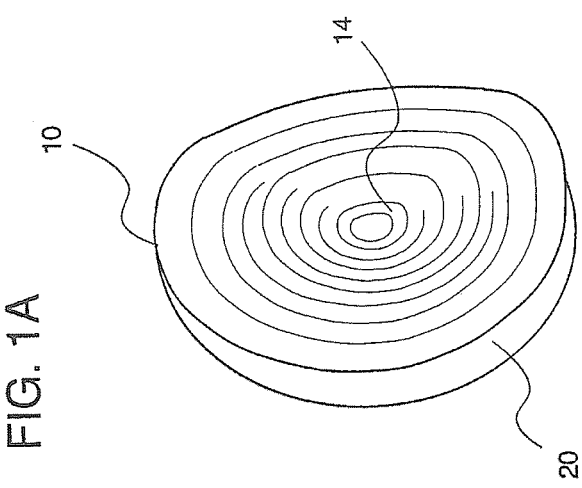
FIG. 1A is an anterior surface view of the circular glenoid implant of the invention.
Figure 3:
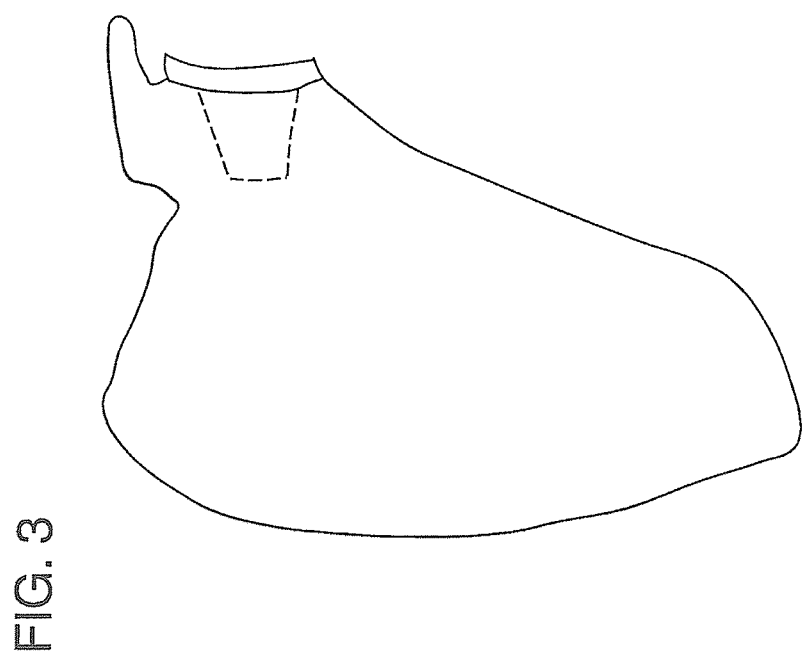
FIG. 3 is an anterior (frontal) view of a typical prior art glenoid implant with a keel design situated in the glenoid.
Figure 4:
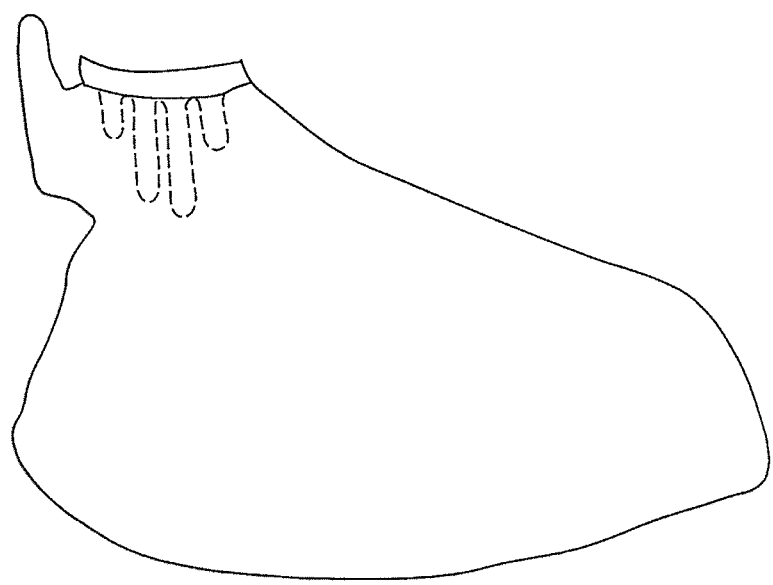
FIG. 4 is an anterior (frontal) view of a scapula containing a typical prior art glenoid implant with a multiple peg design situated in the glenoid.
Figure 5:
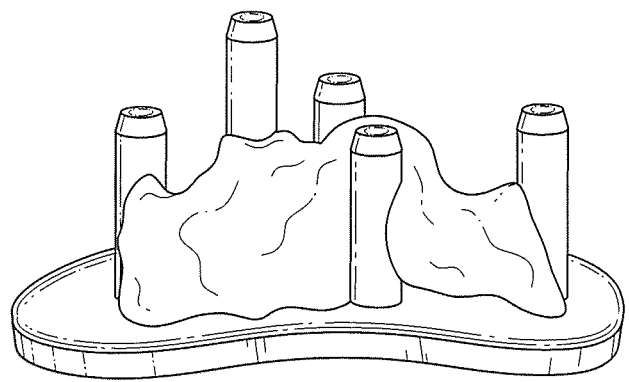
FIG. 5 is a backside view of a scapula containing a typical prior art pegged glenoid implant which was removed from a patient.
Figure 6:
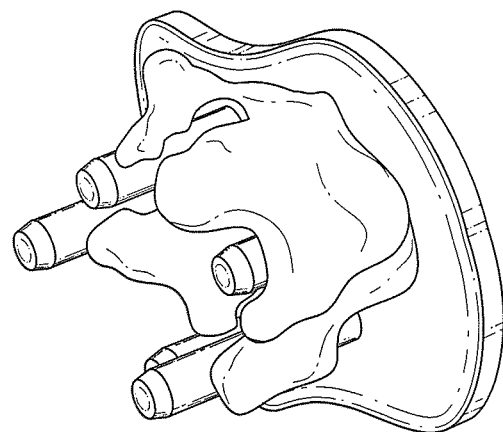
FIG. 6 is a lateral view of the prior art pegged glenoid implant of FIG. 5.
Figure 15:
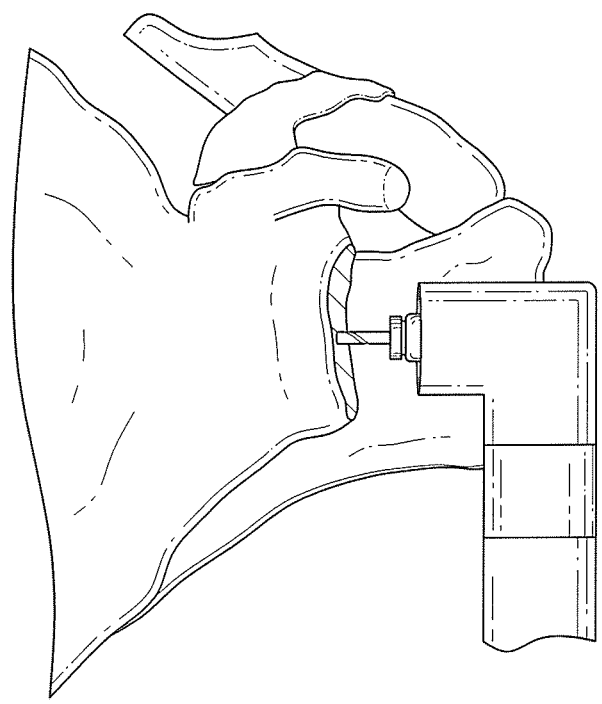
FIG. 15 is an anterior (frontal) view of the scapula showing the use of the 90° drill of the invention.
Figure 16:
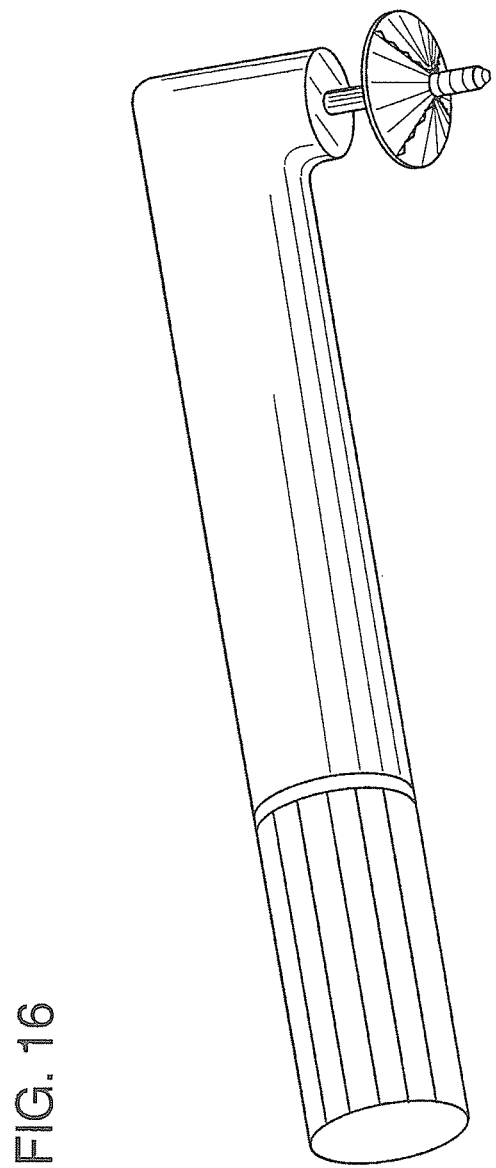
FIG. 16 is a view of the reamer of the invention.

Referring now to FIGS. 1A, 1B, and 1C, there is provided glenoid implant 10, which is intended to be implanted in the glenoid as part of a TSR arthroplasty. Glenoid implant 10 replaces the natural glenoid cavity (see G of FIG. 15) and provides a bearing surface against which the head of a humerus or humeral component may articulate. Glenoid implant 10 includes concave articulating surface 14 and convex or flat backside surface 16, which can, optionally, include roughened or textured surface 18. Glenoid implant 10 can be provided as a circular design (FIGS. 1A and 1C) or as an oblong, oval design (FIG. 1B).

Referring now to FIGS. 2A and 2B, glenoid implant 10 can include short, backside peg 12 on the medial, convex or flat backside surface 16 of glenoid implant 10. Short, backside peg 12 is situated centrally on the medial (back) side of glenoid implant 10 and is preferably a cylindrical peg shape that extends outwardly from glenoid implant 10 away from the back of the implant 16.

Figure 12:
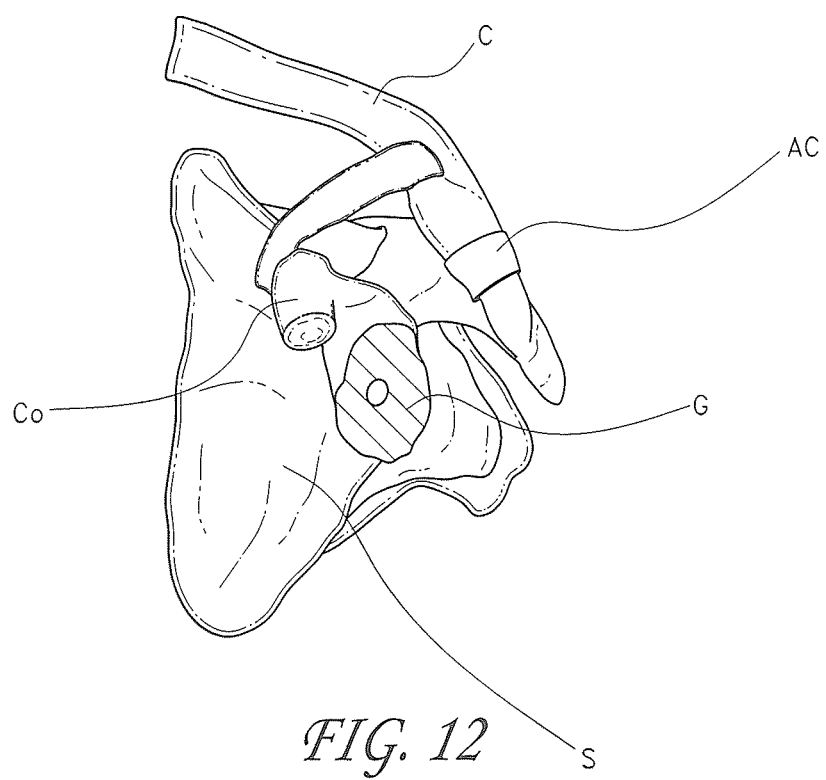
FIG. 12 is a photograph of a model depicting the glenoid (G), scapula (S), clavicle (C), Acromio-Clavicular Joint (AC), and Coracoid (Co). The glenoid is shaded to designate the placement surface for the glenoid implant of the invention.
Figure 13:
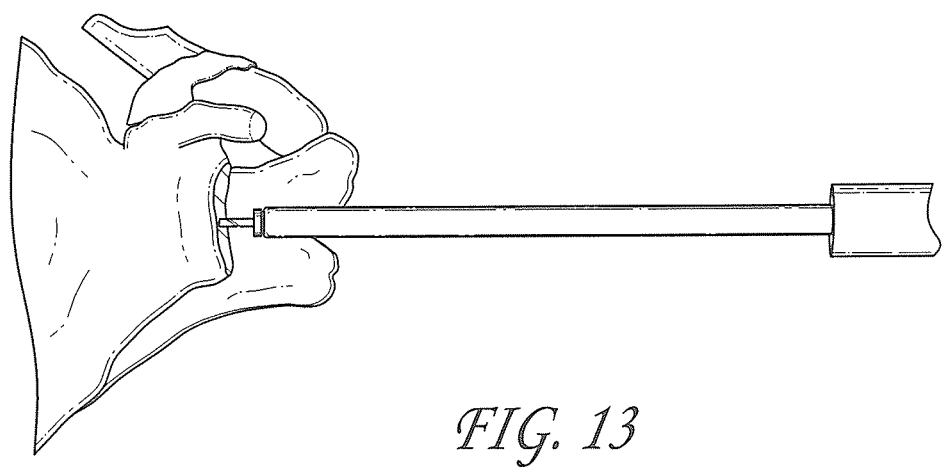
FIG. 13 is a view showing the use of a straight drill of the prior art for preparing the glenoid for implantation.
Figure 14:
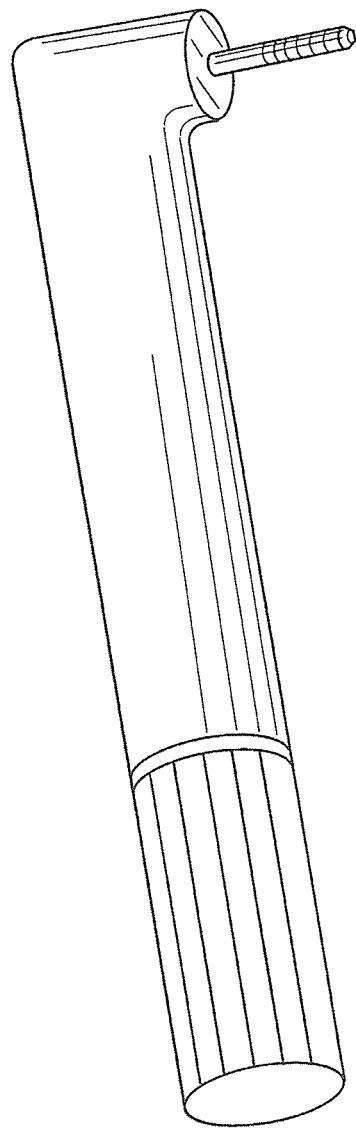
FIG. 14 is a view of the 90° drill of the invention.

Glenoid implant 10, including or excluding short, backside peg 12, is adapted to be implanted in a prepared cavity of the glenoid (see, e.g., FIG. 12), such that it is partially or fully inset to the cortical bone of the glenoid, and is retained with bone cement or using press-fit techniques. Glenoid implant 10 can be further secured to the glenoid using one or more screws.

Glenoid component 10 of the present invention includes concave lateral articulating surface 14 against which the head of a humerus or humeral component moves. Glenoid implant 10 is manufactured using a suitable material, for example, polyethylene, metal, ceramic, or combinations thereof, with lateral articulating surface 14 being smoothly contoured. The radius of curvature of the articulating glenoid surface can match the humeral head surface or it can be slightly larger than the radius of curvature of the humeral head implant.

Figure 32:
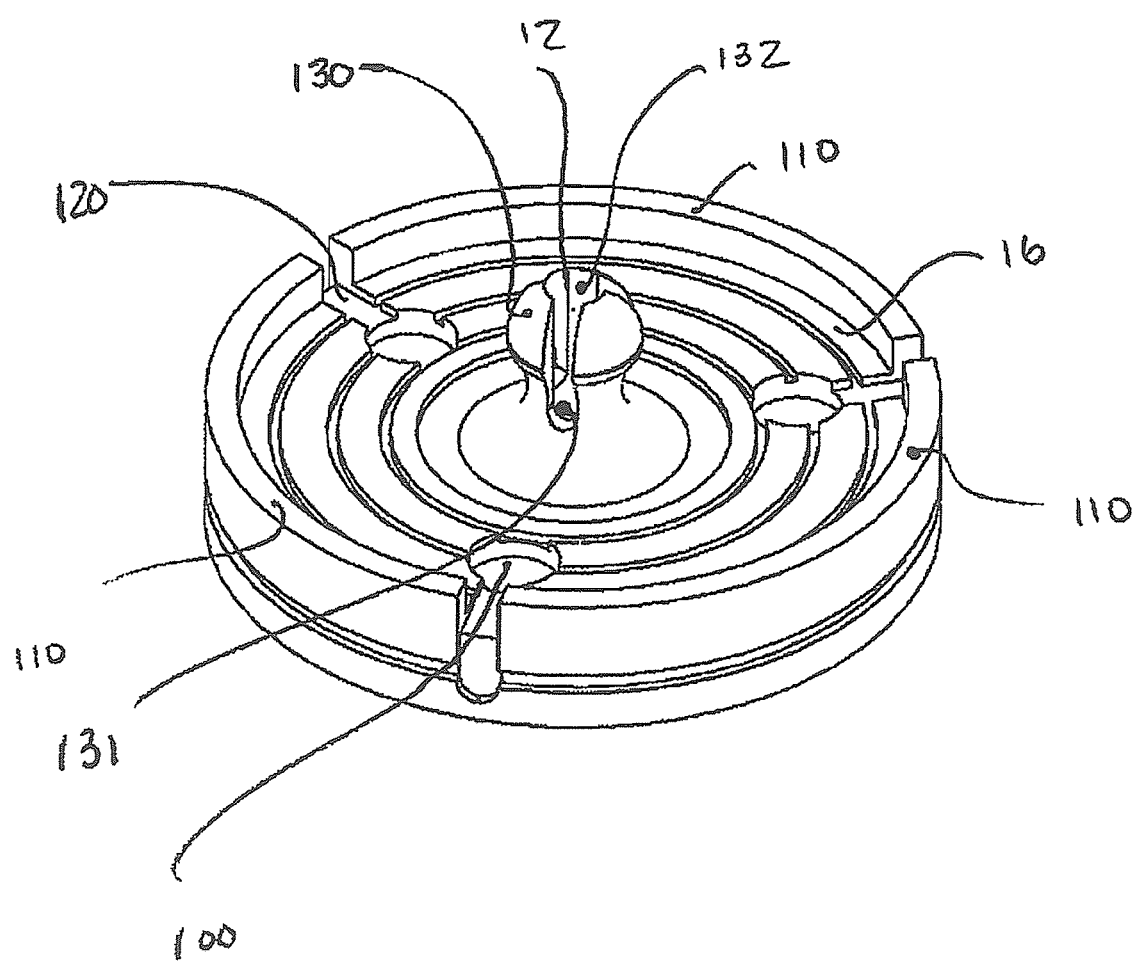
FIG. 32 is a perspective view of the medial aspect of a circular glenoid repair device.

In preferred embodiments, glenoid implant 10 has a lateral articulating surface 14 having a concave circular or oval surface encircled by circular edge 20. The implant at the circular edge 20 has a thickness in an axial direction in the range of about 3-6 mm, preferably about 3 mm. The peripheral edge will have a greater axial dimension in embodiments such as illustrated in FIG. 32 which includes an additional axially extending annular flange.

The medial, back side of glenoid implant 10 is preferably roughened or textured. For example, glenoid implant 10 can include a series of elongated groves 18 in multiple locations for receiving bone cement to assist in the cement augmentation and retention of glenoid implant 10.

In preparing the glenoid to receive glenoid implant 10, the glenoid (G; see, e.g., FIG. 12) is reamed to receive all or a portion of glenoid implant 10 so that glenoid implant 10 is circumferentially surrounded by cortical bone of the glenoid (G), which aids in the stabilization and security of glenoid implant 10.

Referring now to FIGS. 13-16, there will be described a method for preparing a cavity in the glenoid for receiving a glenoid implant of the present invention and apparatus to be used therewith.

In preparing the cavity in the glenoid (G) to receive glenoid implant 10, the surgeon will initially determine the position of the drill site using a guide known in the art (see, e.g., U.S. Pat. Nos. 6,712,823; 6,364,910; 5,030,219; and 5,489,310; all of which are incorporated in their entireties by reference herein).

A reamer of appropriate size is then chosen based on the size of the sizer guide previously chosen. The reamer has a symmetrical head with a plurality of cutting blades and may have a peripheral stop surface. The previously drilled hole is used as a center guide for the reamer. The reamer is used to create a cavity in the glenoid surface of the scapula in which the prosthetic glenoid component will be installed. The reamed cavity is a receiving cavity for the glenoid repair device and is of a geometry that is generally complimentary to the geometry of the medial and peripheral aspects of the glenoid repair implant After the cavity has been created, the glenoid repair device is installed within the reamed bone cavity, with or without the use of bone cement. Insertion may be achieved by manually placing the repair device through the incision into the cavity within the bone or by means of an elongated insertion device so as to permit easy location, guidance and manipulation of the repair device through the incision and into and within the reamed bone cavity.

Figure 26:
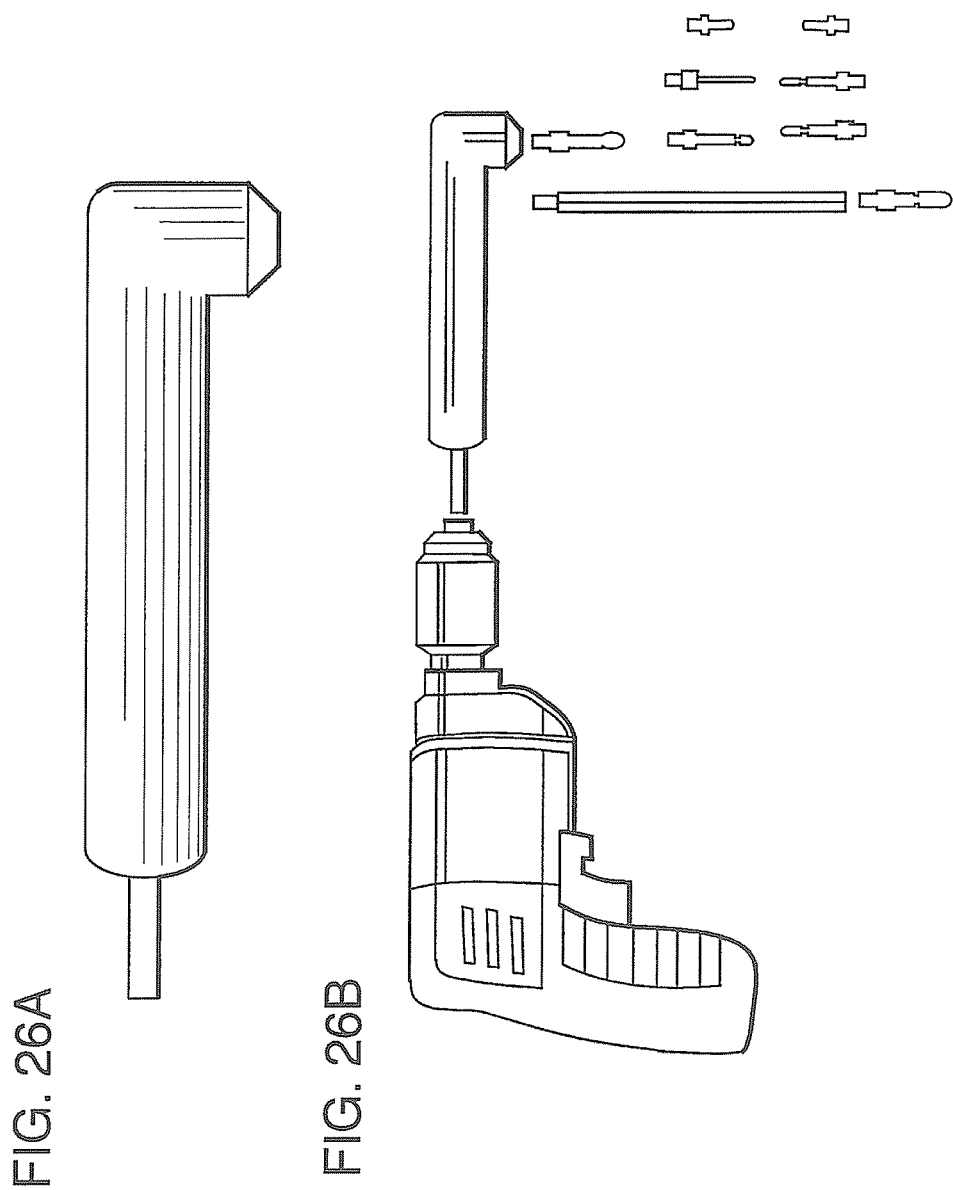
FIG. 26A is a view showing a right angle drill attachment for use in preparing a glenoid for implantation of a glenoid implant.
FIG. 26B is a view showing a drill with the right angle drill attachment and drill bits for use in preparing a glenoid for implantation of a glenoid implant.

A method for implanting glenoid implant 10 will now be described with reference to FIGS. 13-16. Initially, if a total shoulder arthroplasty is performed, a humeral implant having a head portion, discussed below, and a glenoid implant are implanted. Prior to implantation of the humeral component into the humerus, glenoid preparation begins. With the glenoid cavity (G) of the scapula (S) exposed, an alignment or pilot hole is first drilled substantially in the center of the glenoid cavity (G) using, e.g., the drill shown in FIGS. 14, 15, and 26. Once the pilot hole is drilled, the glenoid cavity (G) is reamed using a glenoid surface rasp (see bit attached to the drill depicted in FIG. 16) attached to a reamer shaft with a driver having a laterally directed (e.g. 90°) distal end (see FIG. 26). The glenoid surface rasp may include a guide pin and a roughened cutting surface to create a trough for the glenoid component. The 90° angle of the shaft of the driver permits drilling in tight glenoid cavities. Thus, the procedure can be performed in a minimally invasive manner because it does not require full circumferential exposure of the glenoid, nor does it require a complete capsular release. The 90° shaft of the drill includes a quick-connect attachment which receives the quick-connect drill bit. The reamer is rotated by suitable power means or by hand to ream the glenoid cavity. Following such reaming, the reamer and the guide wire/drill are removed leaving a cavity which is wholly contained within the glenoid cavity (G).

Once the holes have been drilled and the glenoid reamed, a confirmation step is performed in which a provisional or surrogate glenoid implant (often called "a trial") may be used prior to cementing the final glenoid implant to verify placement, range of motion, and glenoid size, and to verify that the glenoid implant is sufficiently inset within the bone. Several iterations of this step may occur, in which various surrogate implant devices are tested in-vivo in order to select a preferred implant geometry. After the preferred glenoid implant has been selected, the surrogate implant is removed. In instances where the surgeon elects to insert the implant within the reamed bone cavity a suitable bone cement, such as polymethylmethacrylate (PMMA) or other compatible material, is placed in the reamed bone cavity of the glenoid vault and may also be applied to the medial (back) surface of glenoid implant 10. Glenoid implant 10 is then positioned within the prepared cavity. If a cemented construct has been chosen, the glenoid implant 10 is then held in place until the cement hardens to assure strong fixation of glenoid implant 10 in the scapula. The head portion of the humerus or humeral component may then engage the concave articulating surface of the glenoid implant 14.

Figure 7:
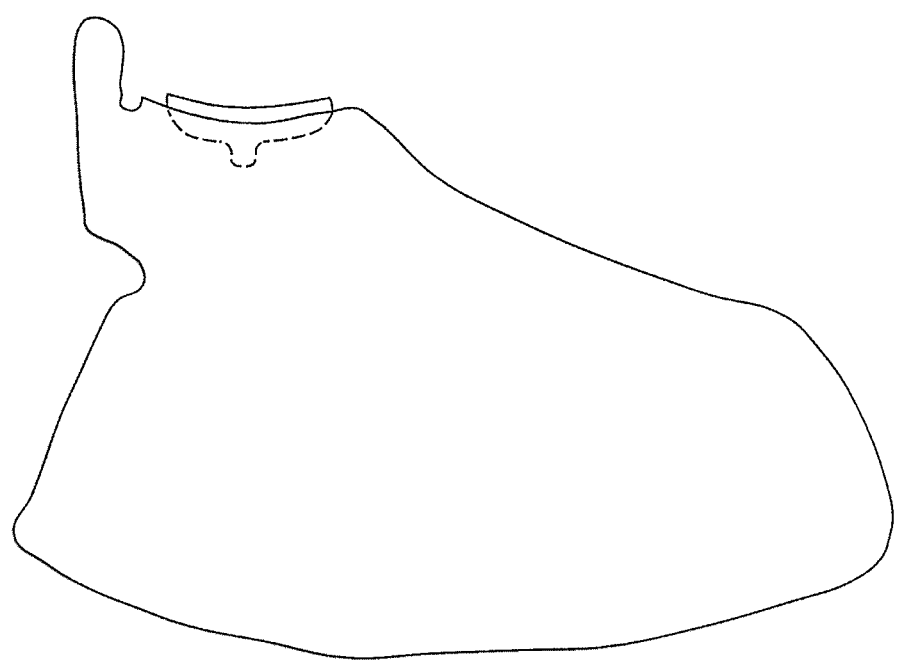
FIG. 7 is an anterior (frontal) view of a scapula containing an inset glenoid implant of the invention situated in the glenoid.
Figure 8A:
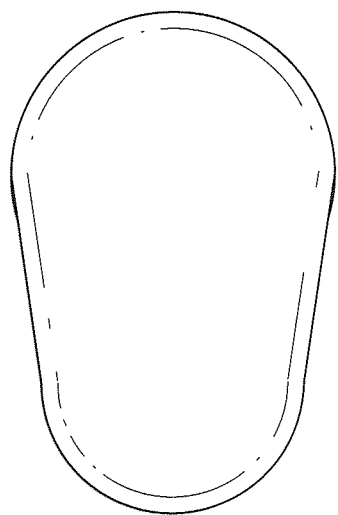
FIG. 8A is an anterior surface view of a typical prior art glenoid implant.
Figure 8B:
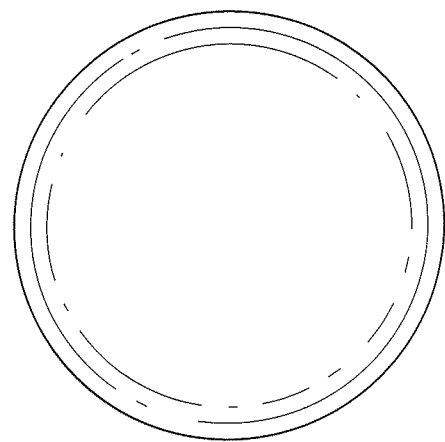
FIG. 8B is an anterior surface view of the circular glenoid of the invention.
Figure 9A:
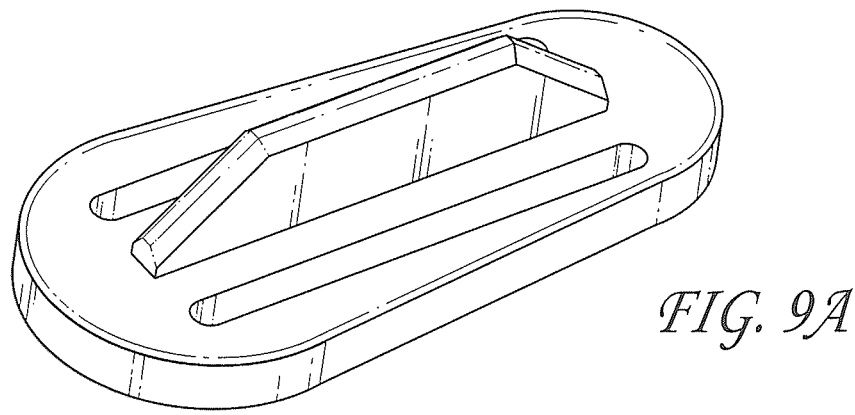
FIG. 9A is a backside view of a typical prior art keeled glenoid trial implant.
Figure 9B:
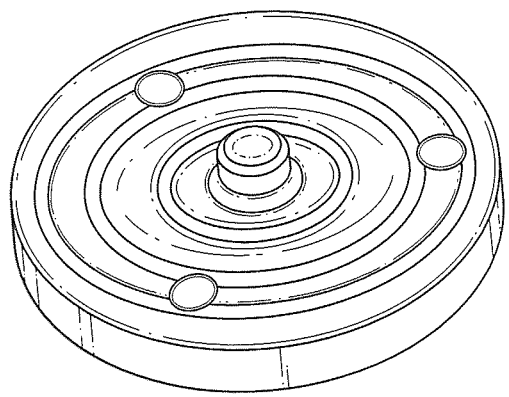
FIG. 9B is a backside view of the circular glenoid of the invention showing a short backside peg.
Figure 10A:
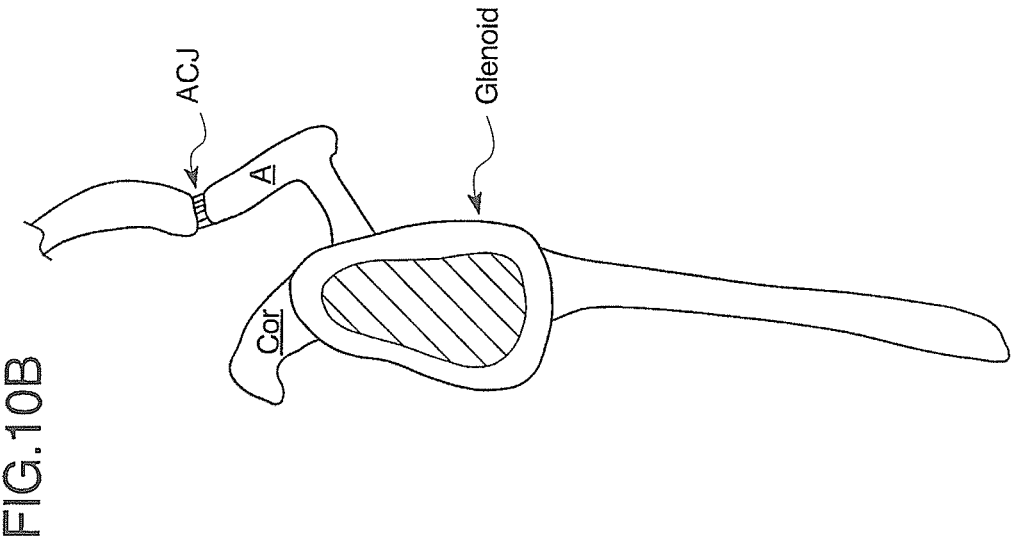
FIG. 10A is a surface view of the glenoid bone with an inset circular glenoid implant of the invention.
Figure 10B:
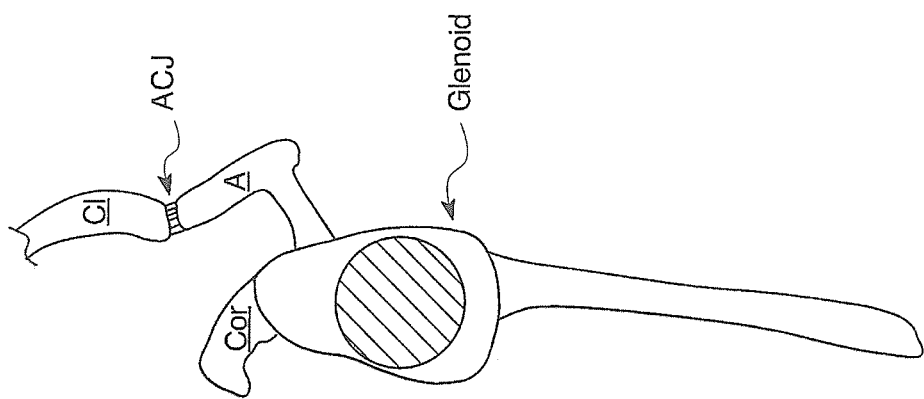
FIG. 10B is a surface view of the glenoid bone with an inset oval glenoid implant of the invention.
Figure 11:
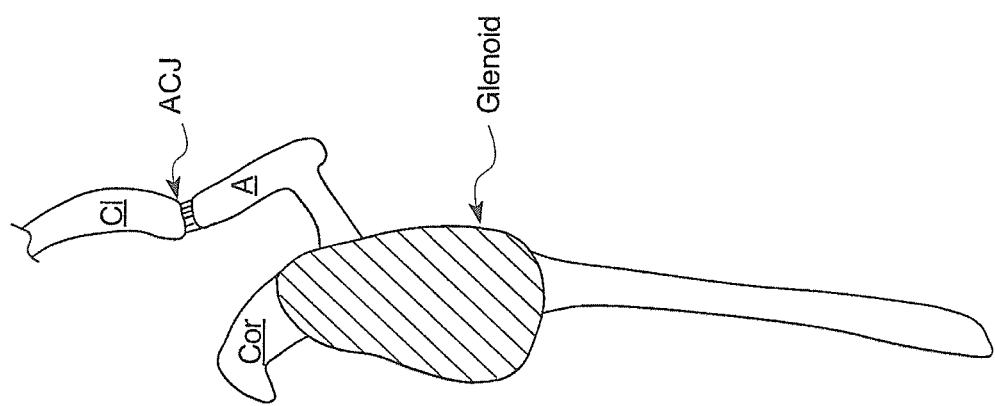
FIG. 11 is a surface view of the glenoid bone with a typical prior art onlay glenoid implant, which does not sit inset to the glenoid bone.

As can be appreciated, the reaming is contained completely within the boundary of the glenoid cavity (G) and therefore does not destroy the peripheral margin of the glenoid surface. Additionally, as can be seen in FIG. 7, there is preferably a slight overhang of glenoid implant 10 beyond the margin of the natural glenoid cavity.

This method can be performed using a deltopectoral or anterolateral surgical approach. For most cases, a limited deltopectoral incision will be adequate to allow exposure to all involved structures. Use of glenoid implant 10 in the shoulder arthroplasty procedure allows the surgeon to use a "mini-incision technique," similar to techniques utilized for total knee surgery and total hip surgery. Typical incision sizes for current Glenoid repair procedures are in the range of 150 mm to 200 mm, use of the methods and devices disclosed herein permits a typical incision size in the range of 70 mm to 100 mm to be used. Further, the use of the glenoid implant 10 reduces the number of surgical steps, entries into the wound and has other surgical benefits as outlined in Table 1. Thus, the glenoid reaming and insertion of the glenoid trial and/or final glenoid implant as described herein may be accomplished via an incision of no more than about 100 mm, preferably no more than about 90 mm and in some embodiments of the invention, no more than about 80 mm.

TABLE 1

Comparison of surgical procedures for Current and Less Invasive Glenoid Replacement

|  | Standard surgical approach | Less invasive Glenoid approach |
| --- | --- | --- |
| Incision size | 15-20 cm | 7-10 cm |
| Deltopectoral incision | Yes | Yes |
| Subscap incision | Yes | Yes |
| Capsule wide incision | Yes | No (only incision of capsule) |
| Labral incision | Yes | No |
| Biceps release | Yes | Only if needed |
| Full inferior capsule incision | Yes | No - partial |
| Axillary nerve dissection - mobilization | Yes | No |

Referring to FIGS. 27, 27A, 27B, 28 and 29, the medial aspect of a glenoid implant device 10 is shown. The device is substantially circular in design, having a radius in the range of about 22 to about 46 mm. Shown also is a central anchor peg 12, the peg having a diameter range of 5 mm to 12 mm and an overall length of less than about 8 mm. The central anchor peg shown has a concave surface 51 disposed to receive a volume of bone cement so as to enhance adhesion and retention of the implant. Alternate configurations of this concave feature may include a plurality of annular ridges or grooves or other negative impressions in the exterior surface of the peg.

In this embodiment the medial surface 16 of the implant device has been configured to facilitate the flow of bone cement across and around the medial and circumferential aspects of said device so as to attain enhanced adhesion and stability of the glenoid implant after insertion into the reamed cavity in the glenoid bone. The medial surface 16 has therein a plurality of concentric grooves 18, and a plurality of radial flow channels 120 disposed to interconnect the concentric grooves forming a continuous flow path between each of the concentric grooves. The interconnecting channels 120 on the medial surface are further connected to one or more circumferentially disposed channels 102 via the radial flow channels 120, thereby forming an open continuous flow pathway from the central anchoring peg 12, across the medial surface of the device 16 to and around the perimeter wall 20 of the glenoid implant device. This interconnected system of concentric grooves 18, radial flow channels 120 and circumferential channel 102 is designed to accommodate the flow of bone cement across the medial surface and around the circumference of the glenoid implant device so as to assure enhanced adhesion of the implant device to and within the reamed glenoid cavity in the bone.

Further illustrated are bone cement wells 100 on the medial aspect of the implant device 16. These wells 100 may be used in conjunction with the interconnected system of grooves 18 and radial flow channels 120 to accommodate and accept any excess bone cement material which may migrate while the glenoid implant device is being compressively inserted into the reamed cavity in the glenoid bone.

Figure 27:
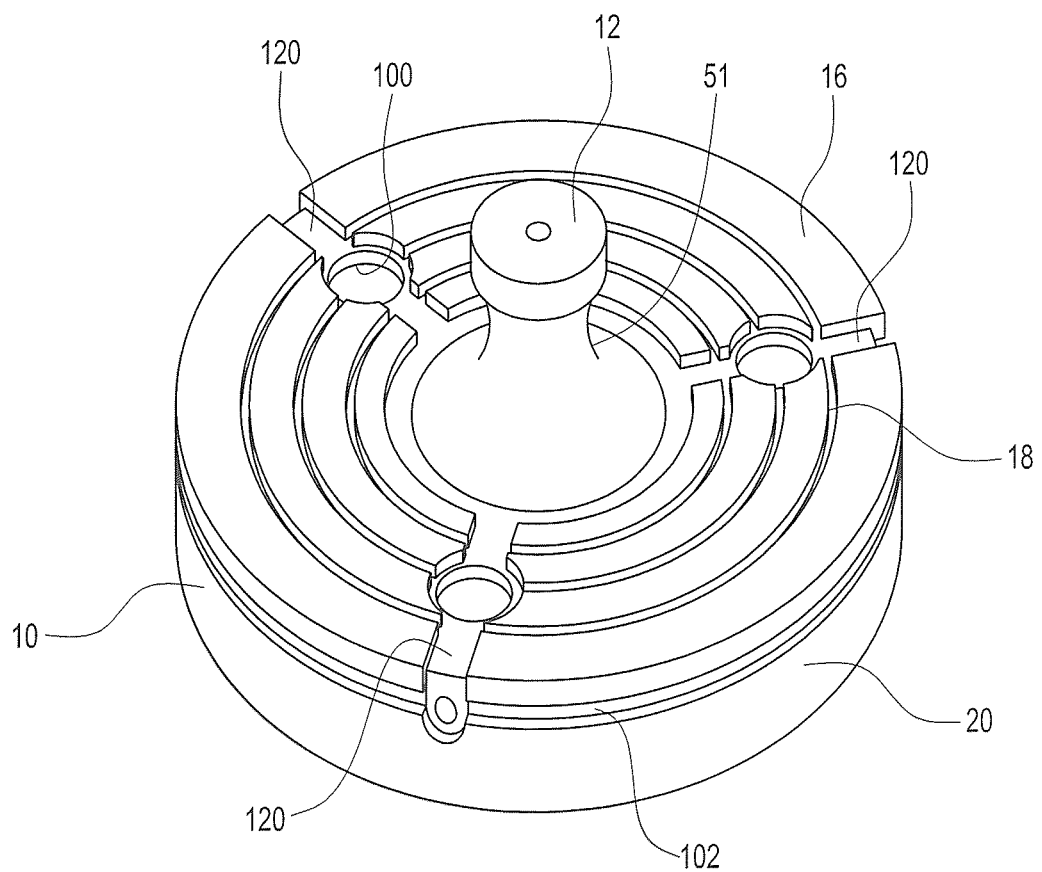
FIG. 27 is perspective view of the medial aspect of a circular glenoid implant, showing a geometry of the medial and perimeter surfaces of the device configured to receive and distribute bone cement.
Figure 27A:
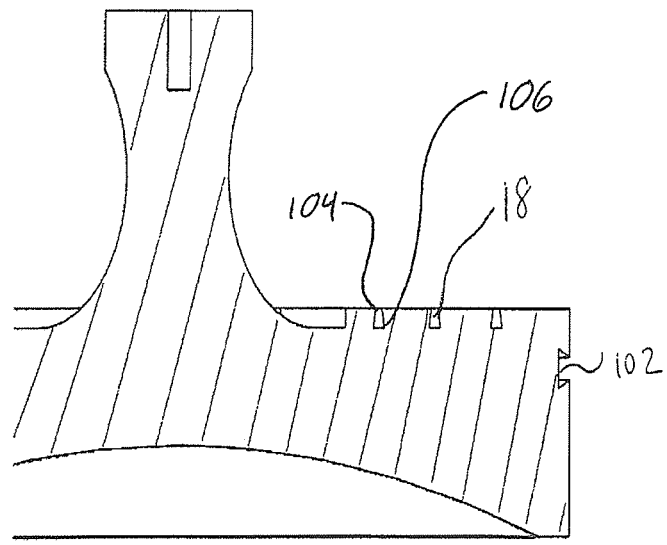
FIG. 27A is a partial cross sectional view of a circular glenoid implant taken along the line 27A-27A in FIG. 27.

While the cross sectional geometry of the flow channel system shown is generally rectilinear in nature it will be understood that various other geometries can be used to further enhance performance, including but not limited to those with negative tapers. FIG. 27A illustrates flow channels with such a negative taper geometry. As illustrated in FIG. 27A, the width of the channel at an opening 104 is less than the width at the bottom of the channel 106. This enables the strength of the bond between the bone cement and the implant to be a function of both the adhesive bonding capabilities of the cement as well as the mechanical interlocking provided by the negative taper.

Figure 27B:
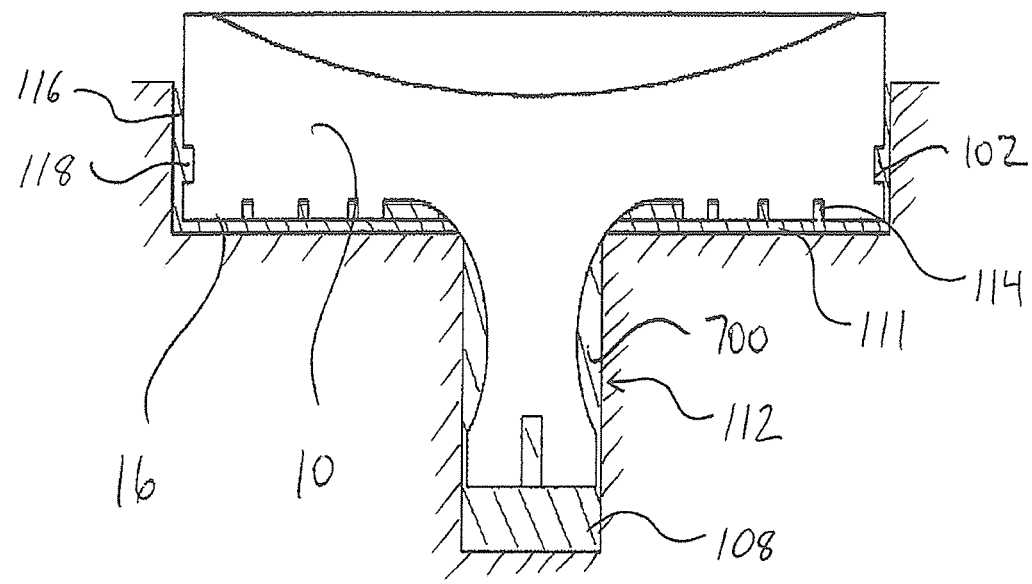
FIG. 27B is a cross sectional view of a circular glenoid implant located within a reamed receiving cavity in bone tissue and being encased and anchored therein by bone cement.
Figure 28:
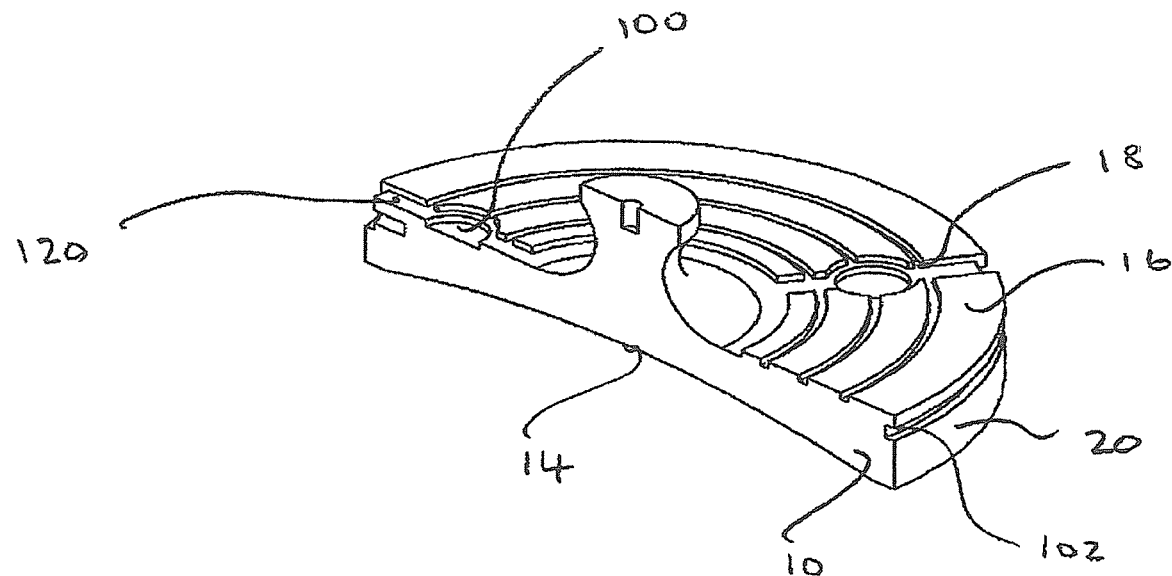
FIG. 28 is a cross sectional perspective view of a glenoid implant, illustrating the interconnected bone cement receiving geometry of the medial and circumferential surfaces.
Figure 29:
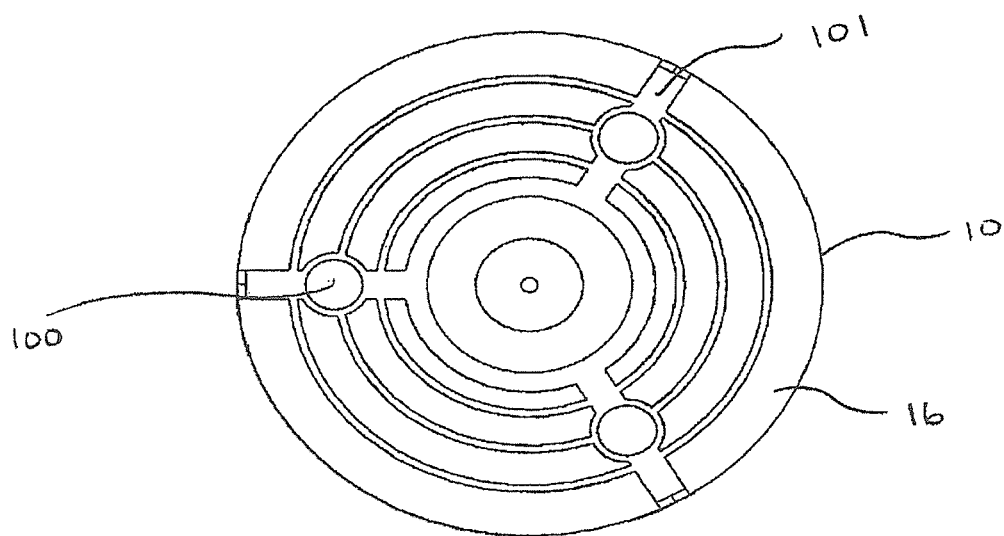
FIG. 29 is a bottom plan view of the medial surface of a glenoid implant, illustrating the interconnected bone cement receiving geometry of the medial and circumferential surfaces.

As illustrated in FIG. 27B, the bone cement 700 following implantation of the glenoid implant 10 will assume a concave configuration in which a first surface corresponds to the medial surface of the implant 10, and a second surface will assume the configuration of the reamed glenoid cavity. The bone cement shell will typically have a first layer 108 extending across the distal end of the central anchoring peg 12. The first layer 108 is connected via tubular wall 112 to a second layer 111. The radially inwardly facing surface of tubular wall 112 will preferably be provided with at least one interlocking engagement structure such as a radially inwardly extending annular ridge (as illustrated) which interlocks with the complementary annular concavity 51 illustrated in FIG. 27. The second layer 111 generally comprises at least one surface structure 114 such as an annular ridge having a complementary configuration to the at least one annular concentric groove 18.

The outer periphery of the second layer 111 is substantially circular in configuration, and carries an outer peripheral annular flange 116. Outer peripheral flange 116 may be provided with at least one radially inwardly directed projection or ridge 118, such as an annular ridge having a complementary configuration to one or more radially inwardly extending annular channels 102 on the perimeter surface 20 of the glenoid implant device.

The hardened cement thus takes on the configuration of a concave shell, which corresponds to the mismatch in size and configuration between the surface of the implant and the complementary reamed surface of the glenoid bone. The thickness of the cement shell may vary, potentially down to zero in spots, depending upon placement and size of the implant relative to its corresponding reamed cavity in the glenoid bone.

FIG. 27B is an illustration demonstrating the adhesion and encapsulation of the glenoid repair implant device 10 within the reamed bone cavity, further illustrated is the bone cement 700, the bone cement adhering to or encapsulating the anchor peg 16, the medial surface of the implant device 16 and the perimeter groove 102.

In certain patients arthritis or other degenerative conditions may have caused substantial wear and degeneration of the glenoid bone structure, resulting in a substantial deficiency of native bone and/or a loss of the natural concave structure of the glenoid joint. As a consequence there may be insufficient native bone remaining to completely engage the circumference of the glenoid implant device using the surgical methods previously described herein.

Figure 30:
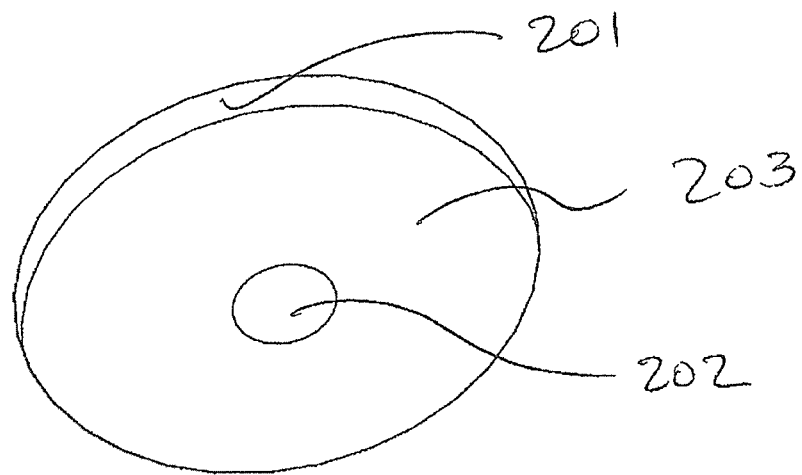
FIG. 30 is a perspective view of a reamed native glenoid bone, showing a reamed cavity within the bone
Figure 31:
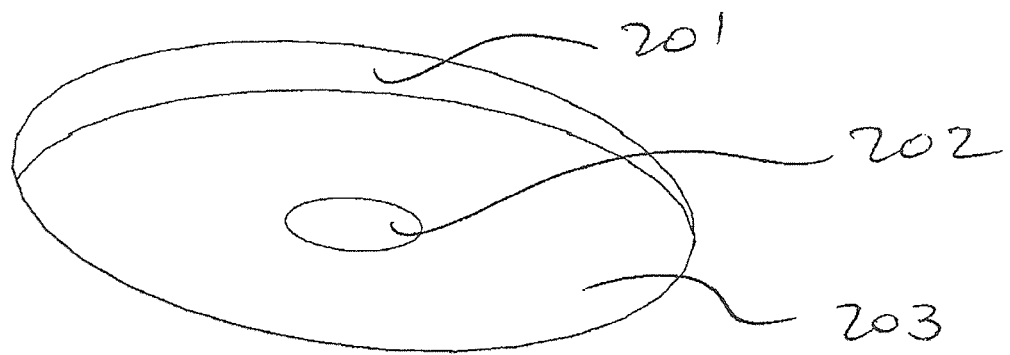
FIG. 31 is a perspective view of a reamed cavity in glenoid bone, the glenoid structure exhibiting bone deficiency.

FIG. 30 illustrates a cavity reamed within glenoid bone, having a reamed surface 203 for engaging the medial aspect of a glenoid repair implant and a perimeter wall 201 completely surrounding the reamed surface 203 for the purposes of circumferentially engaging the complimentary perimeter aspect of said repair implant, thereby encircling and constraining the implant in the reamed bone cavity. FIG. 31 illustrates such a cavity reamed into the glenoid structure of a patient having worn, degenerated or otherwise deficient bone. In this instance there may be insufficient native bone to create a fully enclosed cavity within the bone tissue. As a consequence the reamed surface 203 may not be completely surrounded by the perimeter wall 201. As a result, there may be insufficient native boney structure to assure positive location or fixation of the glenoid repair implant within the reamed bone cavity.

Referring now to FIG. 32, an alternate embodiment of the medial aspect of a glenoid implant device is shown. In this embodiment the medial surface of the device 16 has thereon an axially extending bone engagement structure 110. This structure may be a continuous annular construct such as an axially extending circumferential flange or may be an interrupted or castellated construct as shown. Preferably, the engagement structure 110 will be symmetrically disposed about the circumference of the implant 10 so that the implant may be positioned without regard for its rotational orientation within the bore. Alternatively, the axially extending bone engagement structure 110 may be provided around less than the entire circumference, such as no more than about 270°, or no more than about 180° of the circumference of the implant. Measured in a direction parallel to the longitudinal axis of the post 12, the axial length of the sidewall which includes both engagement structure 110 and the thickness of the implant at the peripheral edge will generally be at least about 3.5 mm, generally no more than about 18 mm and typically within the range of from about 4.5 mm to about 12 mm.

Figure 35:
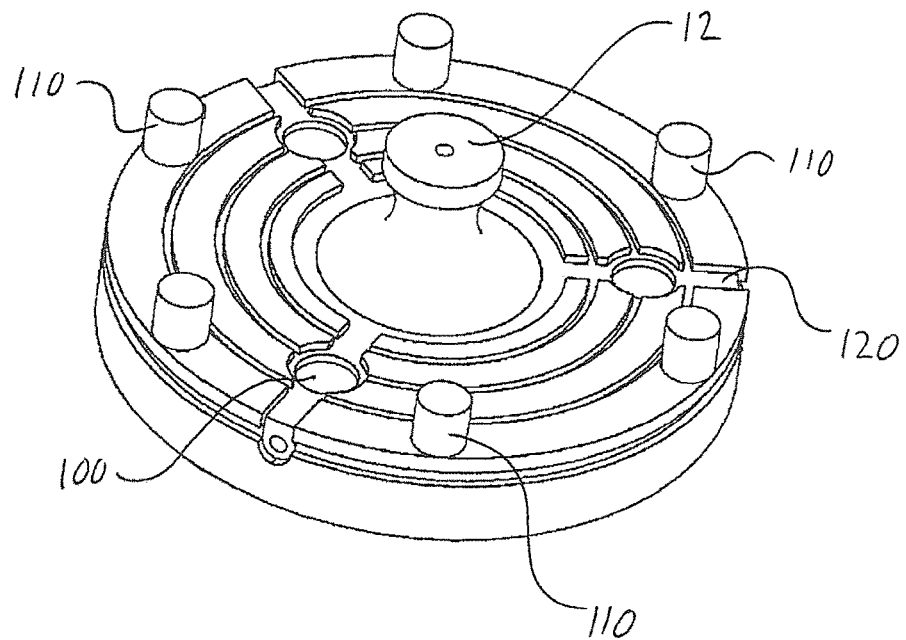
FIG. 35 is a perspective view of an alternate embodiment of the medial aspect of a circular glenoid repair device, having localized protrusions at a radius corresponding to that of the reamed circumferential groove of FIG. 33.

The illustrated engagement structure 110 is positioned at the peripheral edge of the implant 10. However, the bone engagement structure 110 may be spaced radially inwardly from the outer peripheral edge of the implant 110. In general, the engagement structure 110 will comprise either a single annular ridge, or a plurality of projections. See, e.g., FIG. 35. In either event, the engagement structure will generally reside in a concentric circular orientation having a constant radius of curvature from the longitudinal axis of the implant. This permits convenient installation of the implant within a recess formed by a reaming tool having a rotational axis of symmetry. A second or a third or additional axially extending bone engagement structures 110 may also be provided, spaced radially inwardly from the illustrated annular flange.

Figure 33:
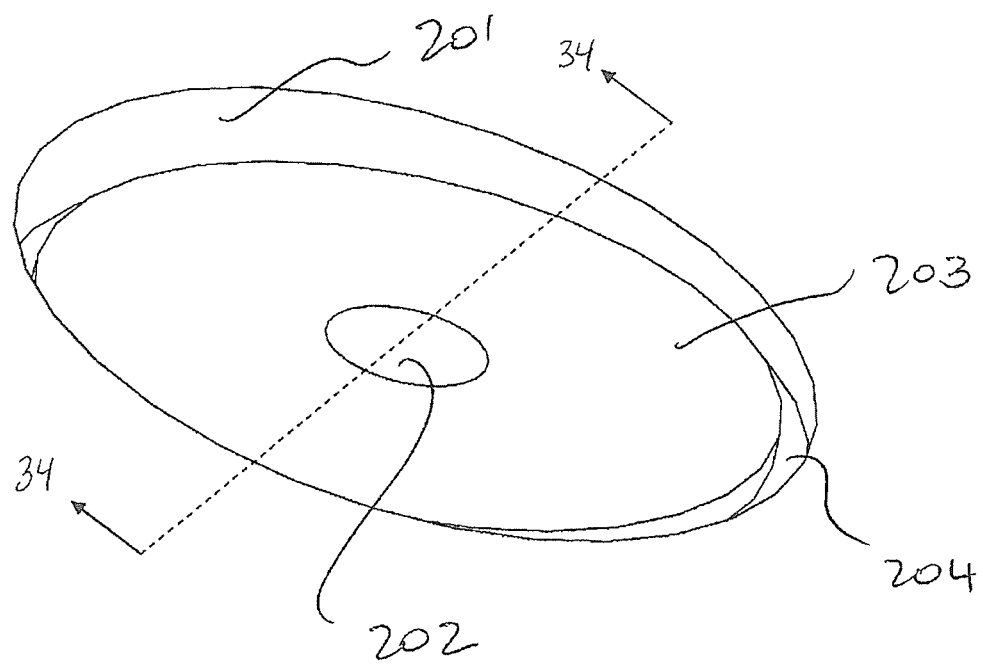
FIG. 33 is a perspective view of a reamed cavity in glenoid bone, the glenoid structure exhibiting bone deficiency.
Figure 34:
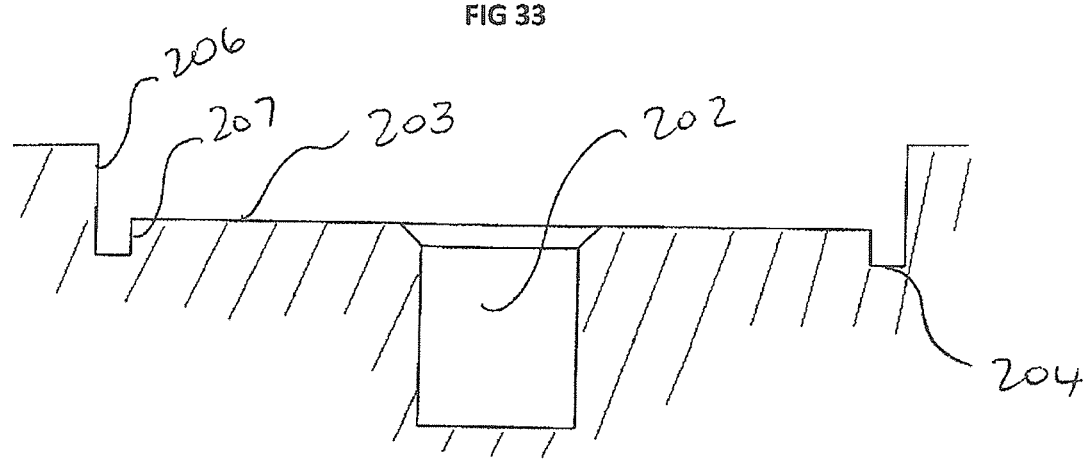
FIG. 34 is a cross sectional view of reamed glenoid bone, showing the view 34-34 of FIG. 33.

To accommodate the embodiment of implant device of FIG. 32 an alternate geometry of the reamed bone cavity may be created. Referring now to FIG. 33 and FIG. 34, this complementary surface structure geometry is illustrated and described in connection with an implant having a single peripheral annular flange bone engagement structure. In this embodiment the reamed bone cavity has a reamed surface 203 disposed to engage the medial surface of the glenoid repair implant. This surface is further provided with a receiving groove 204 reamed below the plane of the surface 203 to receive the peripheral anchor 110 of the glenoid repair implant (see FIG. 32). The groove within and below the surface of the bone tissue may be produced by reaming, either by means of a reamer tool having a complimentary cutting profile which simultaneously produces the surfaces 203, 205, 206 and 207 or by means of 2 reamers, one which produces surface 203, and another which subsequently produces surfaces 205, 206 and 207. The engagement of the perimeter construct 110 of the glenoid repair implant (FIG. 32) with the receiving bone groove 204 within the glenoid bone structure enables complete circumferential engagement of the implant repair device within the glenoid bone structure to assure positive location and engagement of the implant device with and within the native bone tissue. The glenoid repair implant may be fixed to and within the reamed cavity by means of bone cement or other fixation means.

Significant posterior wear and bone loss is common in patients with osteoarthritis, and significant medial wear and bone loss is common in patients with inflammatory arthritis. Combinations of different wear patterns further complicate surgical decision making. Since all current models of glenoid implants lay on the surface of the disfigured, erratic joint surface, it is often impossible to provide secure fixation with current implants that can withstand the stresses of a rotating, elevating, translating humeral head throughout a full array of shoulder motions. Therefore, surgeons often abandon placement of a glenoid implant in deficient bone. In other instances, the surgeon may elect to create a bone graft by cutting out part of the humeral head or resecting hip bone in order to provide a wedge of bone to be secured onto the glenoid bone tissue with screws or other means of fixation. Thereafter, a glenoid implant can be placed through the graft wedge. This procedure is extremely difficult to perform, even by highly skilled surgeon, there is a high degree of subjectivity and the rate of complications is high. Complications may include implant loosening, screw breakage or loosening, graft resorption, neurovascular injury and death.

Further, in patients with substantial bone wear, degradation, or deficiency there may be a need to restore the natural angulation of the articulating surface so as to recreate the natural geometry of the glenoid to humeral interface so as to restore normal mobility and range of motion to the joint. Current practices include the use of a bone graft material in conjunction with prosthetic implant devices, the bone graft material being implanted between the prosthetic and native bone tissue in an attempt to reconstruct the volume and angulation of the bony structure to receive and support the prostheses.

Proposed herein is an alternate embodiment of a glenoid implant device which can be implanted in a minimally invasive manner into bone deficient patients which allows for the restoration of natural angulation and geometry at the humerus to glenoid interface, does not require the use of bone graft material and does not require the use of a long keel or anchor peg system.

Figure 36:
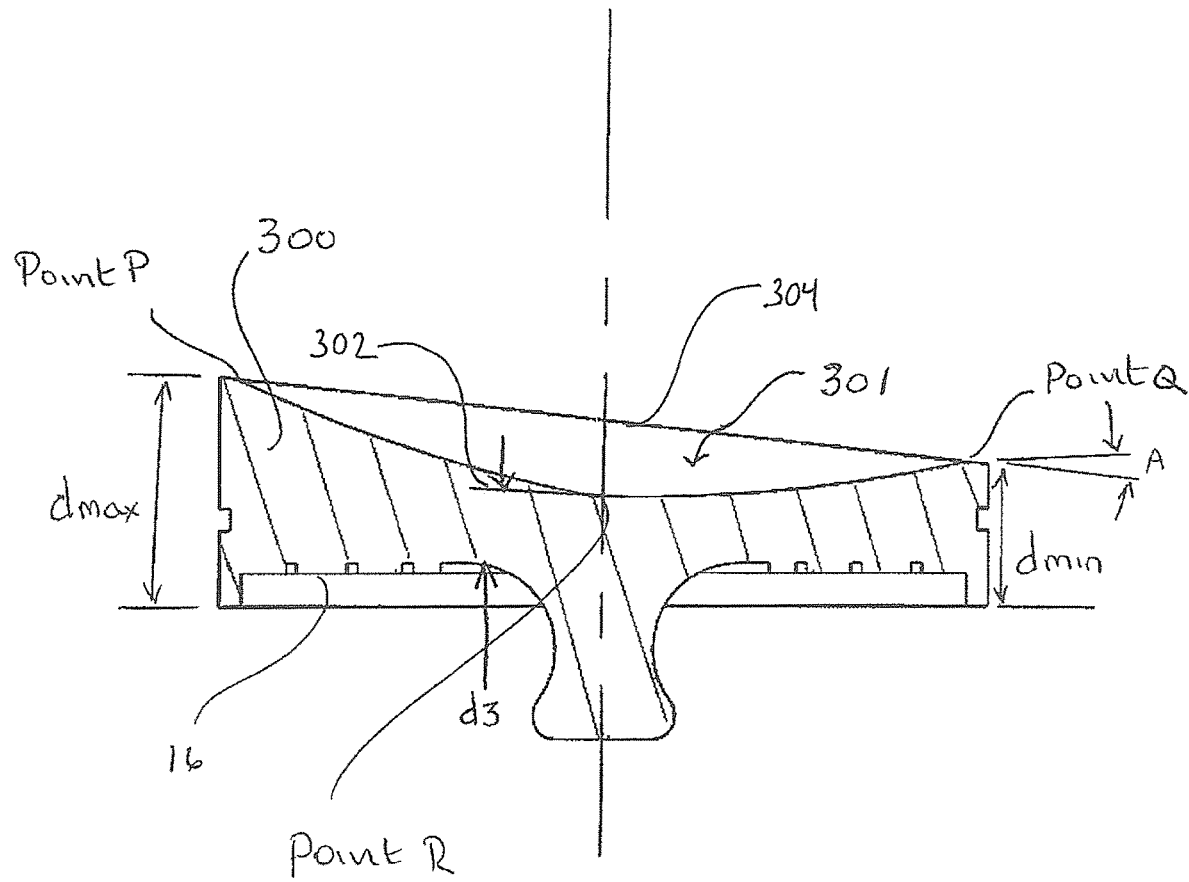
FIG. 36 is a cross sectional view of a circular glenoid implant showing an articulating surface which is offset from the medial surface by an included angle.
Figure 37:
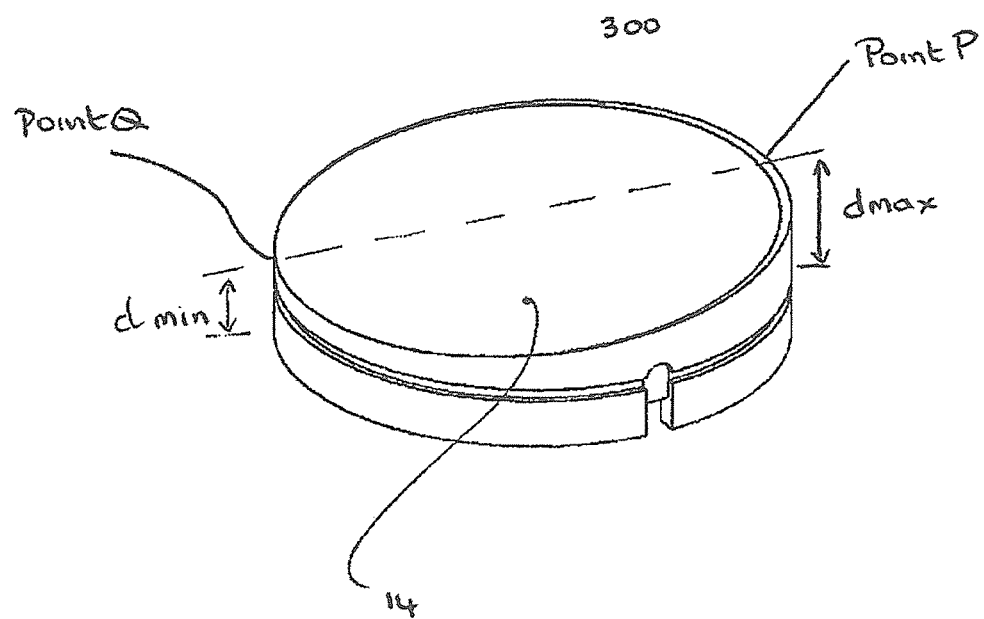
FIG. 37 is a perspective view of a circular glenoid implant showing an articulating surface which is offset from the medial surface by an included angle.

Referring now to FIG. 36 and FIG. 37 a glenoid repair implant device is described, the implant device 300 having a generally cylindrical perimeter concentrically disposed about a central axis which is coincident with centerline CL. A medial surface 16 is configured to contact a reamed surface within glenoid bone and a concave articulating surface 14 is configured to contact the articulating surface of a humeral bone, or humeral bone prosthesis. The 'plane' of the articulating surface 14 is offset from the plane of the medial surface 16 by an include angle A, resulting in a wedge shaped cylindrical form. Angle A represents the corrective angle necessary to restore the functional angulation of the concave glenoid articulating 14 surface with respect to the reamed surface of the cavity within the bone tissue (203) of FIG. 30. Angle A is generally within the range of 5 degrees to 30 degrees.

The position of the neutral or resting position of the humeral to glenoid interface, Point R, may be adjusted by varying the nominal thickness of the implant device, d3 This thickness is typically in a range of 3 mm to 15 mm, depending upon the extent of the deficiency of native bone and the corrective angle necessary to restore functional angulation to the glenoid joint.

Referring specifically now to FIG. 36, shown is a center section view of through a circular glenoid implant. The section view shows the maximum height of the implant Dmax and the minimum height of the implant Dmin, both measured from a common reference such as the medial surface of the implant device 16. The medial surface 16 is perpendicular to the centerline of the implant device CL. The 'plane' of the articulating surface 301 is offset from the plane of the medial surface 14 by the corrective angle A. The offset angle of the plane of the articulating surface, angle A, is defined as the maximum angle created by the intersection of a perpendicular 302 to the centerline of the device CL and the chord line 304 produced by connecting point P and point Q. Points P and Q are the respective maximum and minimum thickness dimension of the implant, measured in an axial direction, at their respective maximum radial distances from the device centerline CL, as measured from a constant reference such as the medial surface of the implant device 16.

Figures 37A, 37B:
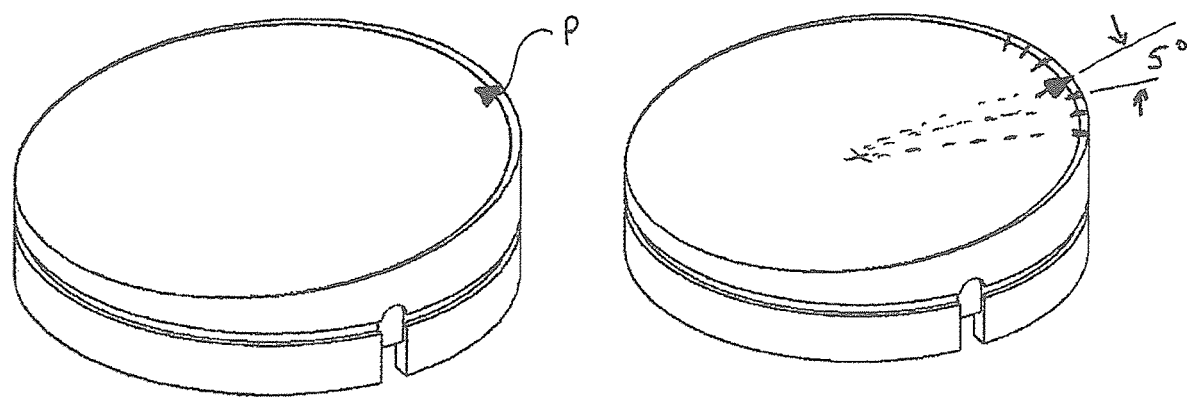
FIG. 37A is a perspective cross sectional view of a circular glenoid implant having an articulating surface which is offset from the medial surface by an included angle, the articulating surfaces having a visible indicator to identify the apex of the articulating surface of the device.
FIG. 37B is a perspective view of a circular glenoid implant having an articulating surface which is offset from the medial surface by an included angle, the articulating surfaces having visible graduated indicia to identify the apex of the articulating surface of the device and to aid in angular positioning of the implant device.

The combination of a circular implant device with this offset angular surface construction enables the surgeon to accurately orient the primary axis of the articulating surface within the wound by rotating the implant device about the centerline of the device CL while it is in-situ in the reamed cavity of the glenoid bone. Referring to FIG. 37A, it is evident that point P can be positioned at any radial location by rotating the implant device about the centerline CL, thereby providing infinite planar orientation of the articulating surface 14 and enabling the surgeon to orient the plane of the glenoid implant so as to optimally restore the functional angulation of the glenoid joint structure.

As an aid to the surgeon, one or more indicator marks can be included on the device, this indicator being visible when the device is implanted within the reamed cavity in the glenoid bone. FIGS. 37A and 37B illustrate alternate embodiments of indicator markings. FIG. 37A illustrates a single indicator mark on the articulating surface and/or the peripheral edge of the implant, which indicates the apex of the articulating surface, point P. FIG. 37B illustrates a plurality of indicia radially orientated around the perimeter of the device, allowing for metered in-vivo rotational adjustment of the device to orient the apex of the implant at the optimal position within the reamed glenoid cavity. Indicia markings may be manufactured by many processes which produce a positive or negative feature on the device or which produce a graphic on or within the device, including but not limited to, laser marking, printing, injection molding and machining.

Figure 38:
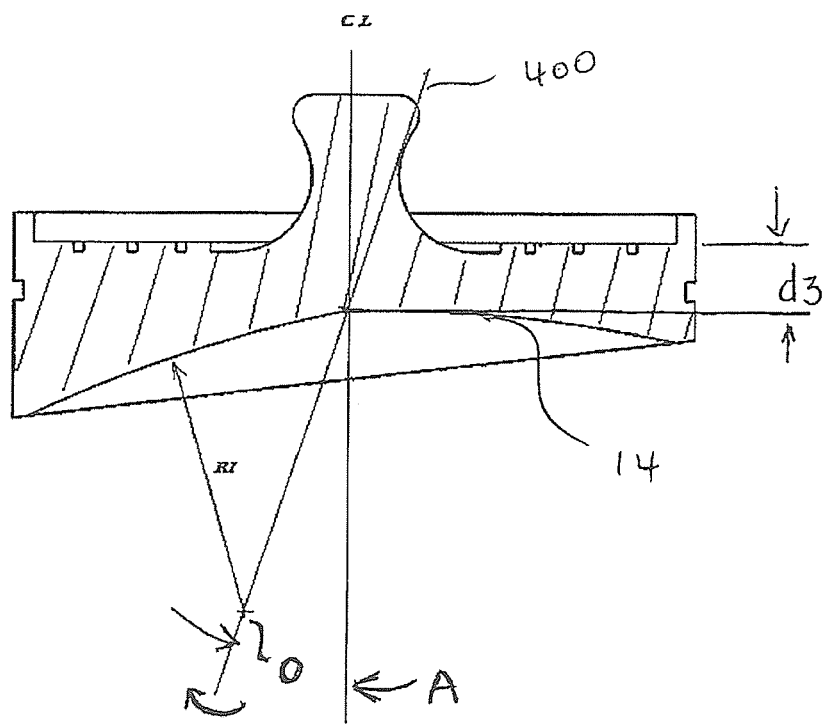
FIG. 38 is an elevational cross sectional view of a circular glenoid implant having offset medial and articulating surfaces and further illustrating an axis of rotation for positioning the implant device within the reamed receiving cavity in the glenoid bone.

Referring now to the embodiment of FIG. 38, the articulating surface 14 is defined as a surface of revolution created by rotating an arc of constant radius R1 about an axis of rotation 400, this axis of rotation being offset from the centerline of the device CL by angle A and intersecting the centerline of the device CL at a prescribed distance from the medial surface D3. In the embodiment of FIG. 38 the radius of the arc of rotation has an origin (O) located on the axis of rotation, thereby producing a spherical articulating surface.

In the foregoing illustration, a line drawn perpendicular to the axis of rotation 400 at the articulating surface 14 (e.g., a tangent) will be angularly inclined relative to the centerline by an Angle A. Angle A may be at least about 5°, 10°, 15°, or 20° or more, depending upon the desired clinical performance.

Figure 39:
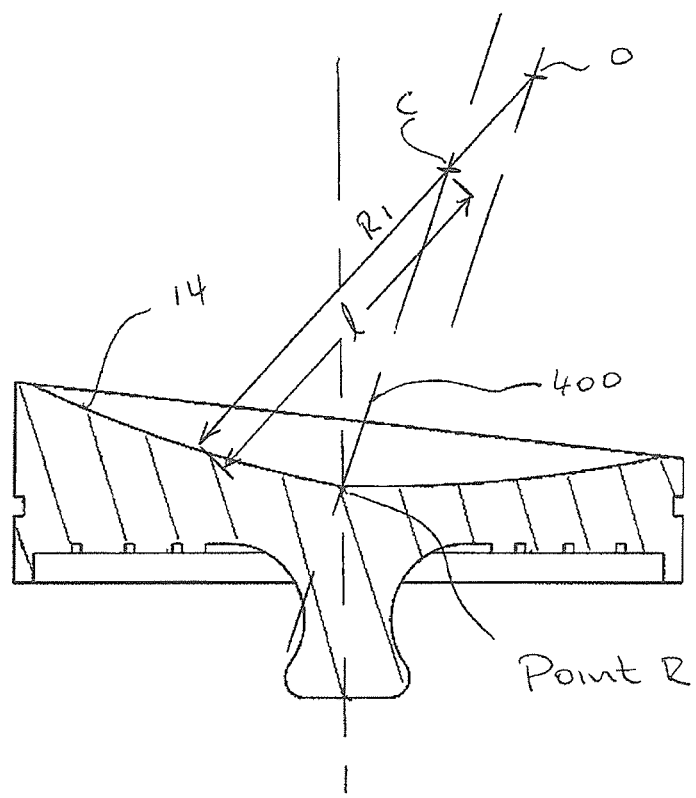
FIG. 39 is an elevational cross sectional view of a circular glenoid implant having offset medial and articulating surfaces, the articulating surface being generated by an arc of constant radius with an origin offset from the axis of revolution, and further illustrating an axis of rotation for positioning the implant device within the reamed receiving cavity in the glenoid bone.
Figure 40:
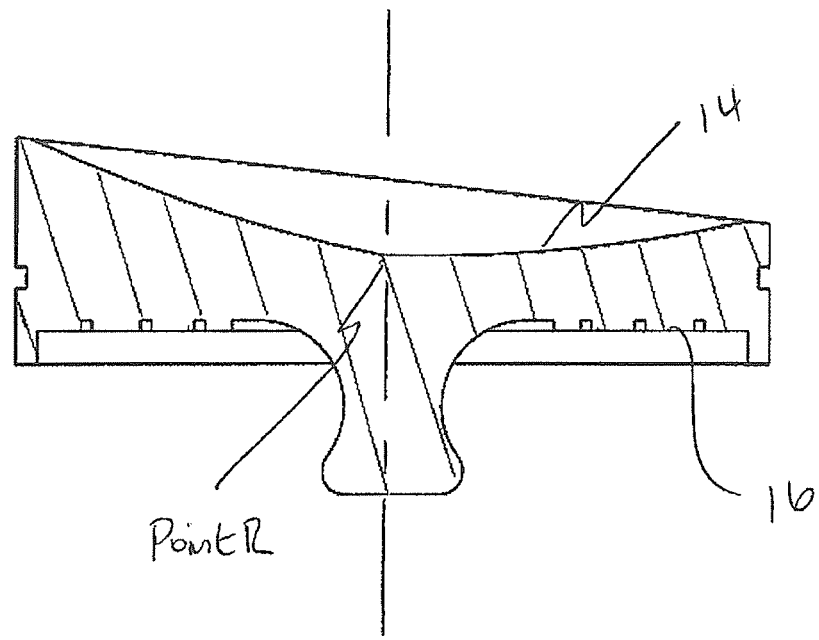
FIG. 40 is an elevational cross sectional view showing the articulating surface resulting from a constant radius arc with an origin offset from the axis of rotation being rotated about the axis of rotation.
Figure 41:
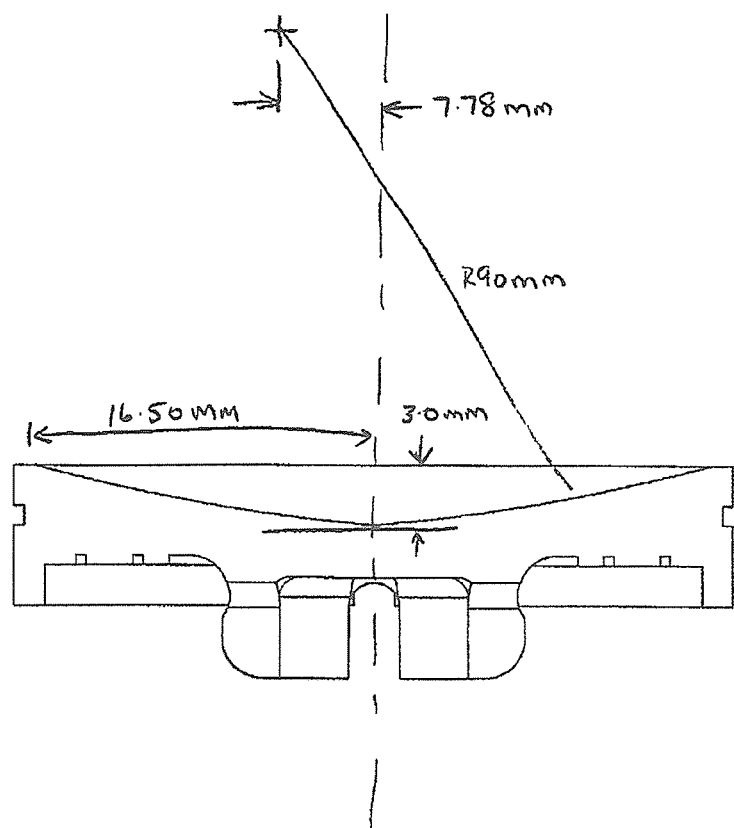
FIG. 41 is an illustration of an exemplary embodiment of an offset surface design.

In an alternate embodiment, shown in FIG. 39, the origin O of the constant radius arc is offset contra-laterally from the axis of rotation 400 of the concave surface. In this embodiment the articulating surface is defined as a surface of revolution, created by sweeping an arc of constant radius (R1) about the axis of rotation 400 to produce a non spherical articulating surface of constant radius R1. FIG. 40 is a side elevational cross sectional view of the articulating surface created by the geometrical construct of FIG. 39, illustrating that the surface construct has an apex at point R. FIG. 41 is a specific embodiment of this construct for a glenoid implant having a cylindrical diameter of 31 mm, the radius of the arc of revolution being 90 mm and being offset contra-laterally from the axis of rotation by 7.78 mm to produce a concave articulating surface with a depth of 3 mm at the device centerline.

In general, glenoid implants in accordance with the present invention will often have a lateral offset distance within the range of from about 2 mm to about 18 mm, and a radius for the arc of revolution within the range of from about 30 mm to about 200 mm and have a circular diameter of 20 mm to 55 mm.

Figure 42:
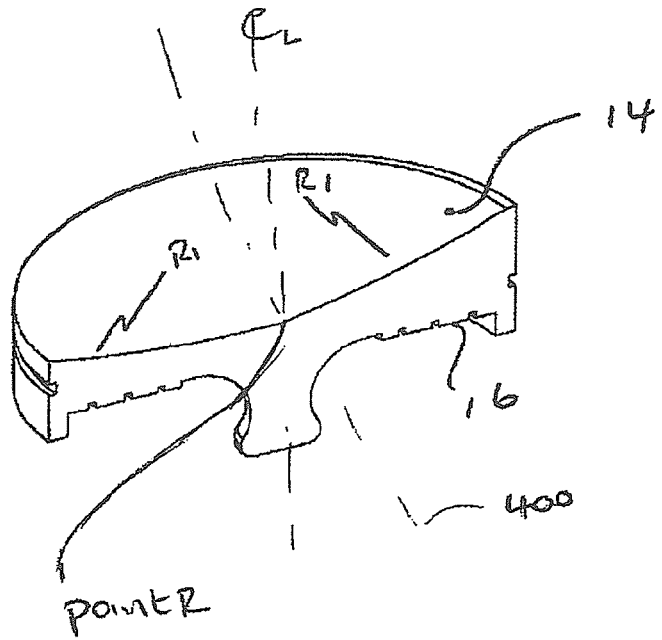
FIG. 42 is a cross sectional perspective view of a glenoid repair device having the plane of the articulating surface angularly offset from the plane of the medial surface, the articulating surface being a non-spherical surface of revolution of a constant radius arc.

FIG. 42 is a perspective view showing a cross section through an articulating surface generated by the specific geometry of FIG. 41, the plane of the articulating surface 14 being offset from the plane of the medial surface 16. FIG. 42 further shows the articulating surface generated by the specific construct of FIG. 41 and identifying the axis of rotation (400), the device centerline CL, the articulating surface of constant radius (R1) created by revolving this arc 360 degrees about the axis of rotation (400) and the resultant apex of the articulating surface, occurring at Point R.

There remains ongoing debate as to the relative benefits of a constrained or non-constrained shoulder replacement system. A constrained system is a specific combination on a prosthetic humeral head and glenoid implant pair, wherein there is a precise and constrained fit between the humeral head and the glenoid implant device, limiting relative motion of the two components to pure spherical articulation. In non-constrained systems the spherical diameters of the humeral head prosthesis and that of the glenoid implant device are deliberately mismatched, the glenoid implant having a larger diameter than the humeral head. In this construct the humeral head can articulate spherically and can translate across the surface of the glenoid implant in an unconstrained manner.

Published literature discusses various biomechanical benefits and limitations of both systems. Both systems offer significant benefits and limitations and several attempts have been made to develop hybrid systems. U.S. Pat. No. 5,928,285 to Bigliani et Al. discloses a system wherein the glenoid surface is defined by 2 or more tangentially intersecting radii, with the central radius being matched to that of the humeral head and the lateral radii of the glenoid being larger than that of the humeral head. The cited benefit being that in the central neutral position the pair acted as a constrained pair and when the humeral head translated laterally onto a glenoid surface of larger radius size than the head, the system mimicked the characteristics of an un-constrained system. In this construct it is necessary to match the humeral head radius to that of the glenoid, thereby requiring that matched pairs be implanted within the patient. U.S. Pat. No. 6,875,234 to Lipman et al. discloses a system wherein the glenoid articulating surface is comprised of 2 non tangential radii, the radius in the central neutral zone being larger than that of the humeral head and the glenoid radius lateral to the neutral zone being of a smaller size and being non-tangential to the radius of the neutral zone. In this configuration the humeral head is free to articulate and translate within the central neutral zone and becomes more constrained as the humeral head translates laterally across the glenoid surface.

Of further note is that fact that in unconstrained systems the contact between the humeral head and the articulating glenoid surface is essentially a point contact. This increases load transfer within and through the glenoid implant and has been shown to negatively impact wear and permits loosening of the glenoid repair implant over time.

Figure 43:
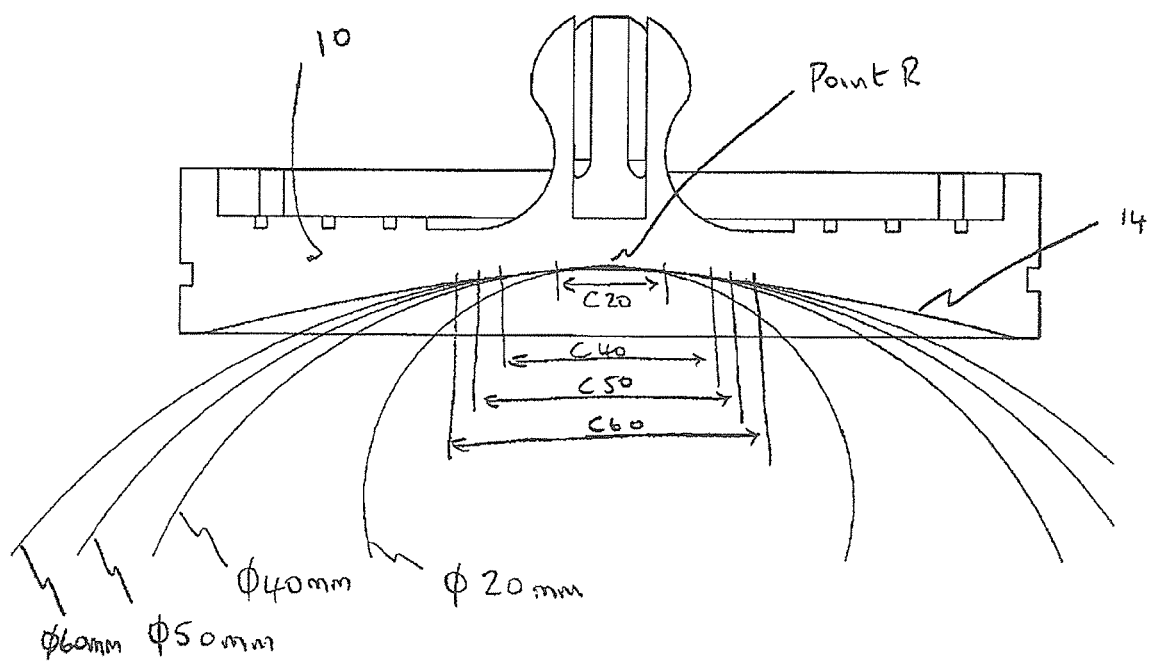
FIG. 43 is a cross sectional view of a glenoid repair device having a non-spherical surface of constant radius, engaging various humeral head configurations.

Referring now to FIG. 43, there is illustrated an enlarged cross sectional view of the articulating surface of the glenoid repair implant construct shown in FIG. 41. FIG. 43 further illustrates a representation of various diameter humeral heads, ranging in size from 20 mm to 60 mm engaging the articulating surface 14 of the glenoid repair implant device 10. Humeral heads in current use range from 36 mm to 60 mm. FIG. 43 illustrates that the geometry of the articulating surface resulting by generating a surface of revolution in a manner described by FIG. 41 can accommodate a humeral head of any size. Further, this offset surface geometry construct results in full circumferential contact between the humeral head and the glenoid articulating surface while in the neutral position. FIG. 43 illustrates the chords C20, C40, C50 and C60 which are the diameters of the circumference of contact between the articulating surface of the glenoid repair device and the corresponding humeral heads having diameters measuring 20 mm, 40 mm, 50 mm and 60 mm respectively. This circumferential contact: 1) increases the surface area of contact between the glenoid surface and humeral head implants significantly, as compared to an unconstrained system with a single point of contact; 2) results in a uniform circular distribution of loads within and through the glenoid implant; 3) distributes loads more uniformly around the central anchor peg so as to minimize offset loads which can loosen the implant; and 4) induces the humeral head to return to the neutral position after any translational movement across the articulating surface 14, resulting in an implant system with self centering characteristics.

In FIG. 43, the geometry of the articulating surface 14 clearly demonstrates an apex of non-contact at Point R. As a consequence of the offset surface geometry construct there is never contact between the humeral head or the glenoid articulating surface 14 in an area of the surface surrounding point R, thereby creating a zone of non-contact having a diameter approximately equal to the chord length discussed above which depends upon the curvature of the humeral head. With this offset surface construct it is therefore conceivable that the articulated surface of the glenoid implant could be discontinuous in this region, allowing for the inclusion of a port or hole passing through the Glenoid articulating surface into the central anchor peg to accommodate secondary fastening or securement of the implant device in the final in-vivo location. Such fasteners could include bone screws, staples, expanding pegs or other axially or rotationally adjustable devices which induce mechanical engagement to the native bone. This construct offers substantial advantage over current devices in which there is contact between the humeral head and any discontinuity in the articulating surface.

Figure 43A:
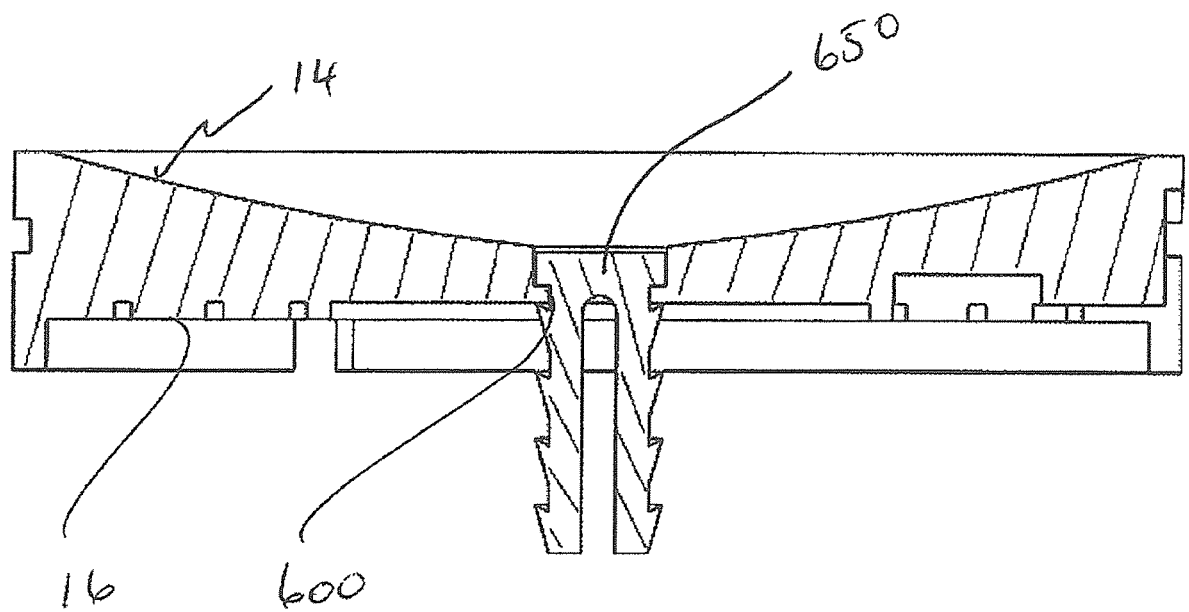
FIG. 43A is a cross section view of a glenoid repair device having a non-spherical surface, the articulating surface having a fixation port between the articulating surface and the medial surface and a mechanical fastener inserted there through into native bone.
Figure 43B:
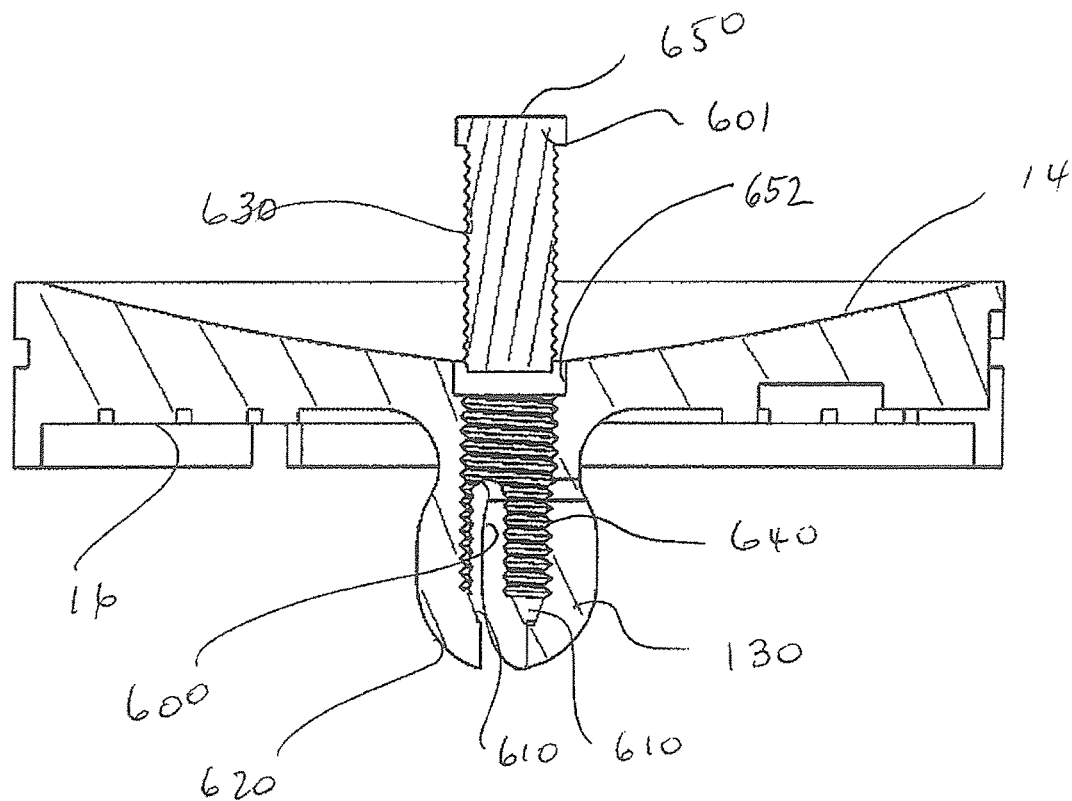
FIG. 43B is a cross sectional view of a glenoid repair device having a non-spherical articulating surface, and a fixation port between the articulating surface and the medial surface, the medial surface including an expandable anchor post with a locking element being inserted into the fixation post through the articulating surface to laterally expand the anchor post elements on the medial surface.
Figure 44:
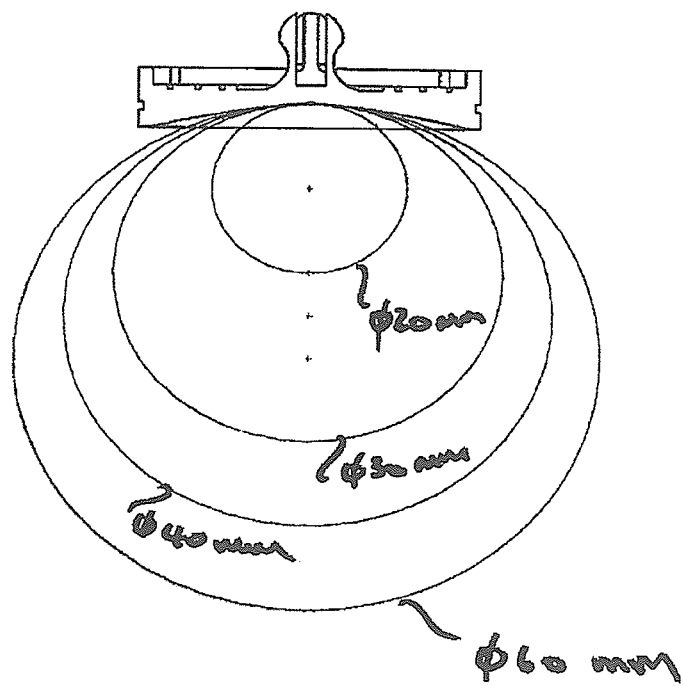
FIG. 44 is a cross sectional view as in FIG. 43, further illustrating the engagement of various humeral head configurations.

FIGS. 43A and 43B illustrate exemplary embodiments of one such construct. In both embodiments there is an open lumen or channel between the offset articulating surface 14 and the medial surface 16, the opening on the articulating surface being located in the zone of non-contact.

The exemplary embodiment of FIG. 43A illustrates a glenoid repair device which does not have an integral central anchor peg. In this specific embodiment the peg is replaced by a removable mechanical fastener 600 such as a bone screw, barbed peg, staple or other device which is inserted through the central access channel into the native glenoid bone passing from the articulating surface 14 through the medial surface 16 and into the native bone structure after the repair implant has been inserted into the reamed receiving cavity in the bone.

Referring once again to FIG. 32, an exemplary embodiment of the medial aspect of a glenoid repair implant device is shown. In the configuration shown a segmented central anchor peg is shown, having an annular construct with a hollow core 132 and the annular aspect being divided into a plurality such as two or three or four or more discrete axially extending finger elements 130. In this embodiment the external diameter of the anchor peg (E) is larger than the internal diameter of the corresponding receiving hole drilled in the native glenoid bone. Upon insertion of the anchor peg into the receiving hole the finger elements 130 flex elastically radially inwardly into the hollow core 132 producing a radially outwardly directed compression force to be exerted in the native bone tissue. Such a segmented construct can be mechanically enhanced and complimented by a mechanical feature which engages the finger elements or native bone within or through the hollow core 132.

Referring now to FIG. 43B in combination with FIG. 32, the exemplary embodiment illustrated in FIG. 43b has an open access channel 600 between the articulating surface 14 and the medial surface 16 of the device and further passing axially through the segmented central anchor peg, the segmented anchor peg being of a construct similar to that illustrated in FIG. 32. A mechanical fastener 601 is inserted in an axial direction through the opening of the central access channel 600 at the articulating surface of the implant device 14, engaging the internal surfaces of the anchor peg segments 610. As the fastener progresses axially into the channel, the anchor peg segments 130 are induced to flex radially outwards causing the external surfaces of the anchor peg segments 620 to impinge into the native cancellous bone of the glenoid structure below the cortical bone surface. This impingement anchors the implant within the native bone of the glenoid structure. The radially outwardly facing surfaces of the segments 620 may be provided with any of a variety of barbs, ridges, roughened surface textures or other bone engagement feature.

The mechanical fastener illustrated in FIG. 43b is a threaded device, having an external thread 630 which mates with an internal thread 640 within the glenoid implant device. Various embodiments of the mechanical fastener 601 may be used, including but not limited to, screws, barbed rods and split pegs.

The mechanical fastener 601 includes a proximally facing surface 650, which, following installation, will face the humeral ball. Surface 650 is preferably recessed beneath the adjacent articulating surface 14. This may be accomplished by providing a recess 652 into the articulating surface 14 to receive a head on which the surface 650 resides. Alternatively, the mechanical fastener 601 may comprise a threaded body having a relatively constant outside diameter throughout its axial length, such that it can be axially advanced into the access channel 600 until the proximally facing surface 650 is beneath the level of articulating surface 14.

In an embodiment in which mechanical fastener 601 is rotated into engagement with segments 610, the proximal surface 650 is provided with a mechanical interfit coupling, for removably cooperating with a driver tool. The coupling may comprise a recess such as slot or polygon such as a triangle, square, pentagon or hexagon. Implants in accordance with this aspect of the invention may be provided in a kit which includes a driver tool, such as an Allen wrench, or other specialized screwdriver to rotationally engage the mechanical fastener 601. The driver tool may comprise an elongate tubular body, having a lateral bend such as a 90° bend at its distal end. A rotatable tip is carried by the distal end, and configured to complement the geometry of the engagement structure on mechanical fastener 601. The rotatable tip is connected via the central lumen to a proximal control, which may be rotated by the clinician to rotate the mechanical fastener 601 into place. Mechanical connection between the proximal control and the distal rotatable tip may comprise a flexible cable extending through the central lumen, or a torque rod which may be provided with suitable gears at the point of the bend to translate rotational force from the longitudinal axis of the tool to the transverse axis of the rotatable tip.

In general, any of a variety of structures may be utilized to convert axial proximal or distal movement, or rotational movement of an active engagement mechanism, to produce a radially outwardly directed advance of one or more bone engaging components carried by the post 12, to facilitate bone engagement.

Figure 45:
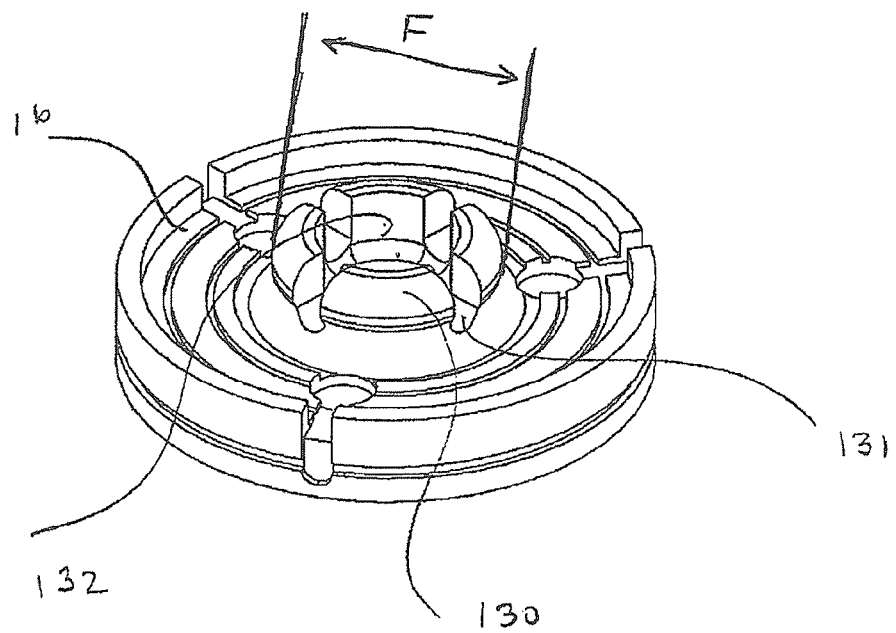
FIG. 45 is a perspective view of the medial aspect of a circular glenoid repair device, showing an alternate implementation of the central anchor peg.

Referring now to FIG. 45, an alternate embodiment of the medial aspect of a glenoid repair implant device 16 is shown having yet another exemplary embodiment of a segmented central anchor peg construct. In this embodiment the central anchor peg has an external diameter F, within the range of from about 10 mm to 20 mm. The relatively wide anchor peg is intended to isolate and distribute the forces transmitted to the glenoid implant device by the humeral head while articulating within the normal neutral region of the shoulder joint.

The segmented anchor peg of this embodiment may further be provided with a hollow core 132, capable of accepting and retaining supplemental bone graft material so as to promote osteointegration of the glenoid repair implant within the native bone. Radially outwardly actuatable barbs, spikes or other bone engagement structures may also be provided as discussed above.

Referring now to FIGS. 43 and 45 in combination, a specific embodiment of a glenoid repair device is described, the device having an offset articulating surface construction of FIG. 43 combined with the large diameter anchor peg construct of FIG. 45. In this embodiment, diameter F of the glenoid repair implant (FIG. 45) is larger than the maximum chord of contact which can occur for the corresponding humeral implant thereby assuring an optimal distribution of forces within the glenoid repair implant as a result of the circumferential line of contact and optimal transfer of loads through the glenoid repair implant into the native bone structure through the structure of the central anchor peg.

Humeral Head Cutting Jig

Figure 17:
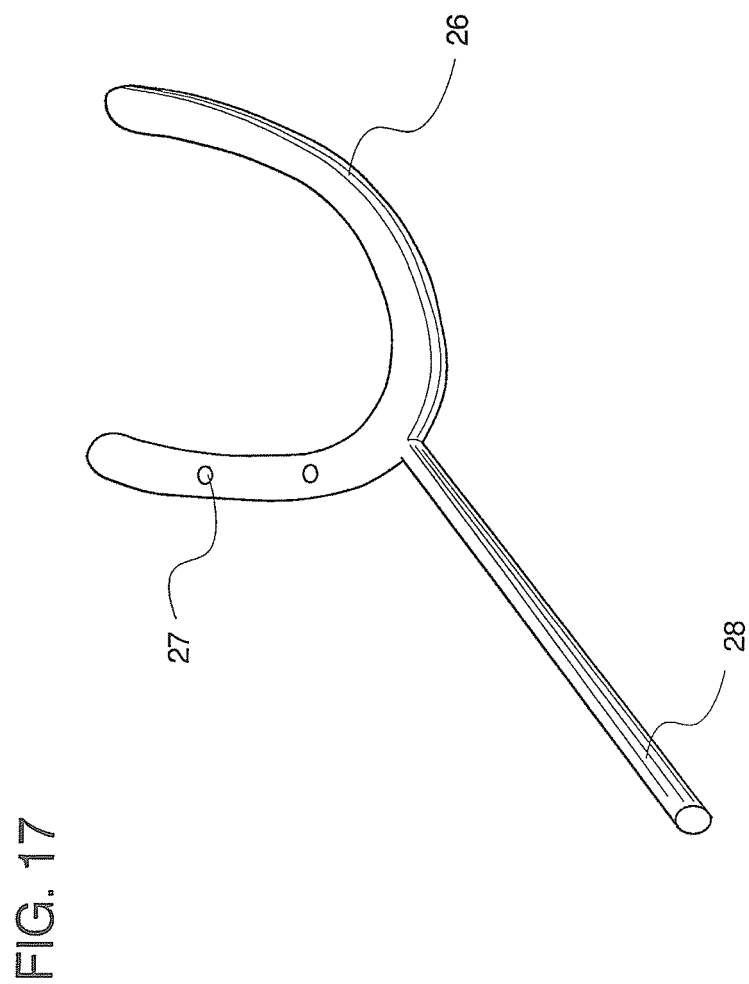
FIG. 17 is frontal view of the humeral cutting jig of the invention
Figure 18:
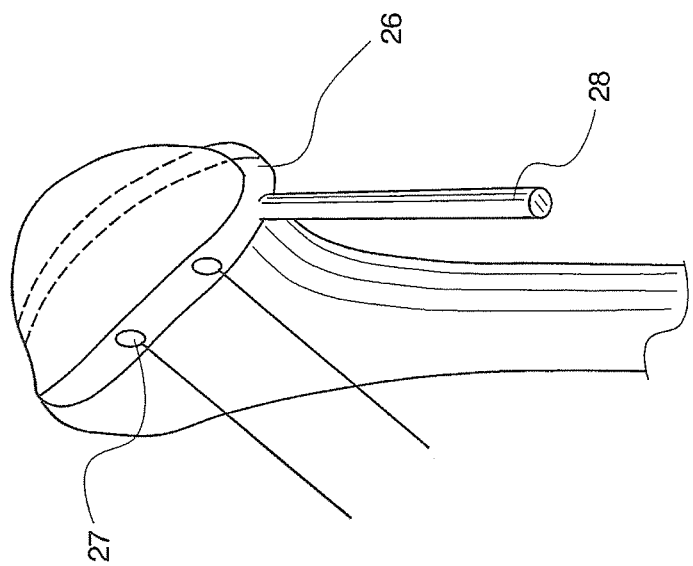
FIG. 18 is side view of the humeral cutting jig of FIG. 17 placed in position on a humerus. The cutting jig can be secured by K-wires (shown), pins, or screws.
Figure 19:
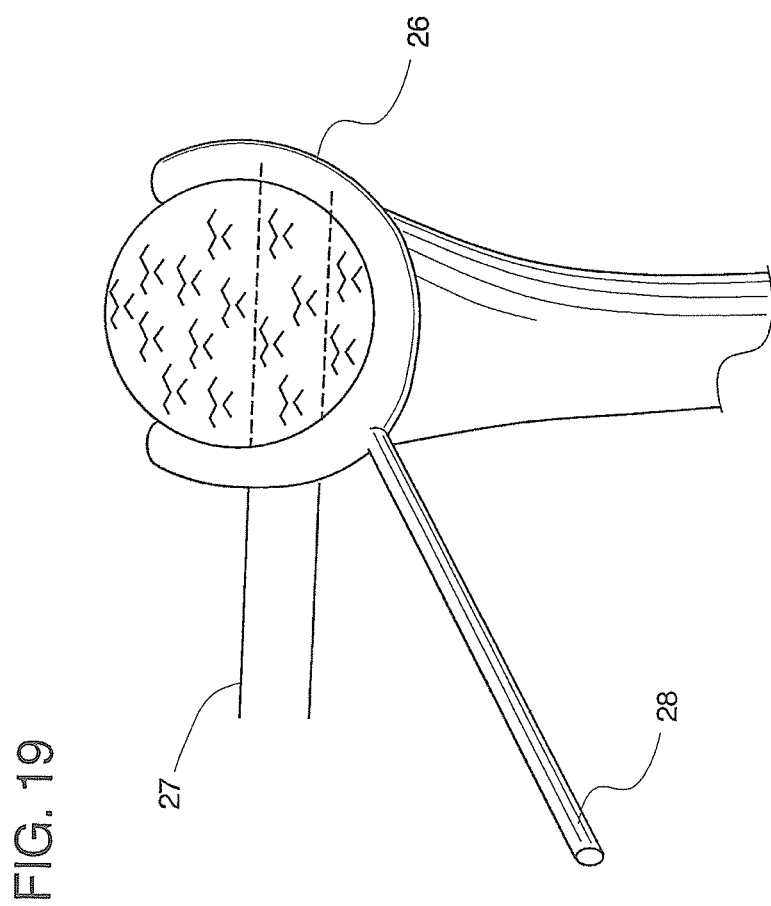
FIG. 19 is a view of the humerus and humeral cutting jig of FIG. 18 after resection of humeral head along the axis of the cutting jig.
Figure 20B:
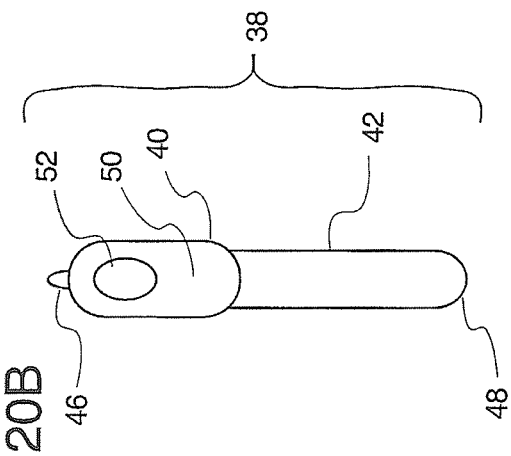
FIG. 20B is a lateral view of the humeral implant of the invention.
Figure 20D:
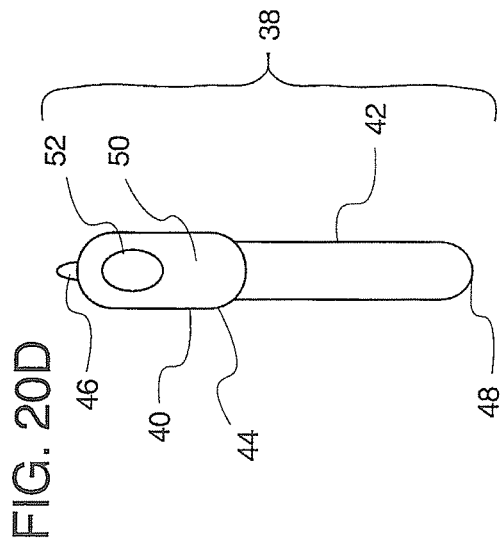
FIG. 20D is a lateral view of the humeral implant of the invention with a collar.
Figure 20A:
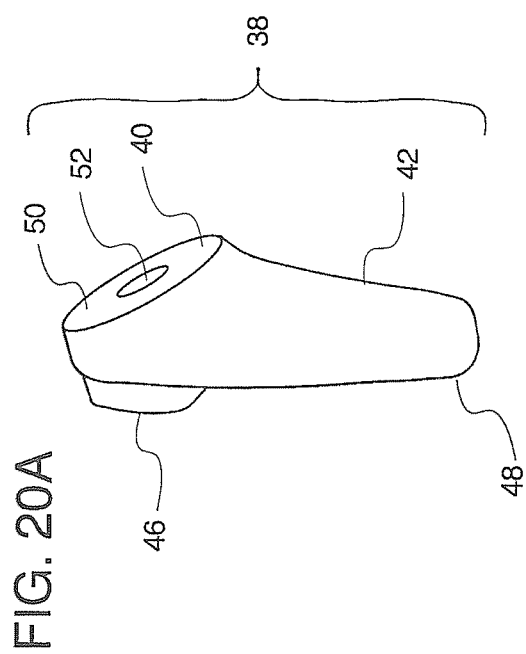
FIG. 20A is an anterior (frontal) view of the humeral implant of the invention.
Figure 20C:
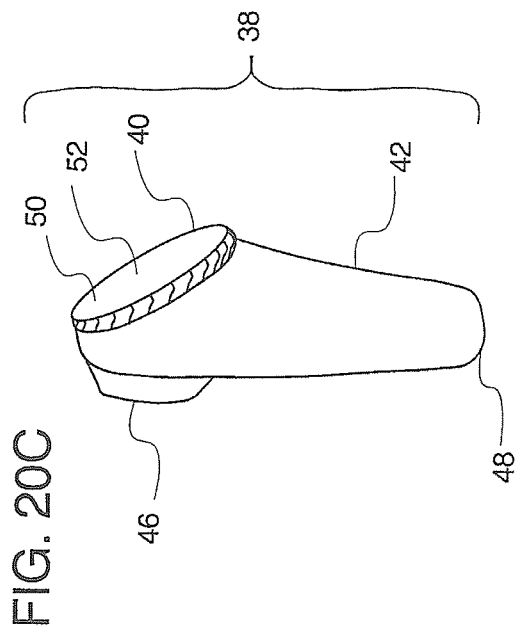
FIG. 20C is an anterior (frontal) view of the humeral implant of the invention with a collar.

Referring now to FIGS. 17-19, humeral head cutting jig 26 according to the present invention is a simple, low profile humeral cutting jig that can be a full circle or part thereof. Cutting jig 26 can be secured to the humeral head using K-wires, pins, or screws 27 and is removed after completion of humeral head resection. Cutting jig 26 includes handle portion 28.

The cutting jig should be placed along the anatomic neck of the humeral head. Osteophytes which obscure the junction of the humeral head and humeral shaft should be removed in order to accurately mark the level of the anatomic neck circumferentially from anterior to inferior to posterior. The cutting jig can be fixed to the humerus using wires, pins, or screws at the appropriate angle and version as determined by the surgeon. The rotator cuff should be carefully protected with retractors, and then the humeral cut is performed using an oscillating saw or osteotome along the surface of the cutting jig.

The cutting jig can be manufactured using metal.

Humeral Implant

Referring now to FIGS. 20A-D, humeral implant prosthesis 38 according to the present invention includes stem 40 having elongated portion 42 optionally including collar 44, which prevents humeral implant prosthesis 38 from embedding too deeply in the humerus. Humeral implant 38 also includes flange (fin) 46, which aids in the fixation of the stem in the humerus and prevents rotation of humeral implant in the humerus. There may be just one lateral flange (fin), or there may be two or three flanges (fins), e.g., with one lateral, one anterior, and one posterior. The stem length is preferably less than about 70 mm, and the stem width is preferably less than about 40 mm (preferably about 30 mm).

At the distal end of the stem, there is rounded portion 48 and at the proximal end of the stem is a support surface extending radially from the stem. The support surface has an upper planar surface 50 that includes bore (hole with morse taper) 52 extending inwardly from the top plane thereof, and which is adapted to be engaged by a humeral head implant with a morse taper extension. Modular humeral head implants (both concentric and eccentric) are known in the art (see, e.g., U.S. Pat. Nos. 4,865,605; 5,314,479; 5,462,563, and 5,489,309, and U.S. Patent Application Nos. 2004/0167629, 2004/0064187; each of which is incorporated herein by reference). The plane of upper planar surface 50 is preferably between about 45 degrees and about 60 degrees to the axis of the stem.

The entire stem portion, or a portion thereof, is preferably coated with a porous material for aiding in the fixation of the humeral implant in the humerus for a press fit stem. The implants made for cement fixation can have a smooth surface or a roughened, textured surface.

Humeral implant 38 can be rectangular or rounded edges, but is significantly thinner anterior to posterior than medial to lateral. It will have a morse taper for securing a standard humeral head implant.

An advantage of the humeral implant of the present invention over current humeral implant stems is that the humeral implant of the invention is significantly shorter than most current stems, which are about 70-115 mm in length. Because the humeral implant is shorter, it saves bone because of the narrow metaphyseal area required for implantation. The present humeral implant is less than 70 mm in length, preferably about 60 mm in length, and less than 40 mm anterior-posterior width (preferably about 30 mm). Fixation of the present humeral implant depends upon good interference fixation in the medial-lateral plane when press fit (similar to some current total hips). The humeral implant can be fixed using a bone cement, such as polymethylmethacrylate (PMMA) or a compatible fixation material, or it can be press-fit.

The invention will now be described by the following examples. The following examples are meant to illustrate the invention. They are not meant to limit the invention in any way.

EXAMPLES

Example 1

A 62 year old woman presented with progressive, debilitating shoulder pain from osteoarthritis, which she had experienced for approximately 15 years. She had constant pain (rated 9/10) and difficulty washing her hair, fastening her bra, lifting a cup of coffee, and performing other daily activities. The preoperative radiographs and CT scan showed severe shoulder arthritis and glenoid bone loss that would preclude the use of a keeled or pegged glenoid implant. There was concern that a hemiarthroplasty procedure (replacement of the humeral ball, which would leave the arthritic glenoid socket bare) would not relieve the patient's pain.

A total shoulder replacement using an inset glenoid implant of the invention and a standard humeral implant was performed. The smaller size and circumferential fixation of the inset glenoid implant allowed safe placement of the prosthesis within the confines of the patient's deficient glenoid cavity.

The deficient glenoid vault was not fractured and the fixation was very stable. The patient had 100% relief of pain only 1 week after surgery. Her own assessment of shoulder function 4 weeks after surgery was 56% of normal (American Shoulder and Elbow Society validated outcome score [ASES score]) was 56 compared to 16% of normal before the surgery (ASES score 16).

Figure 21:
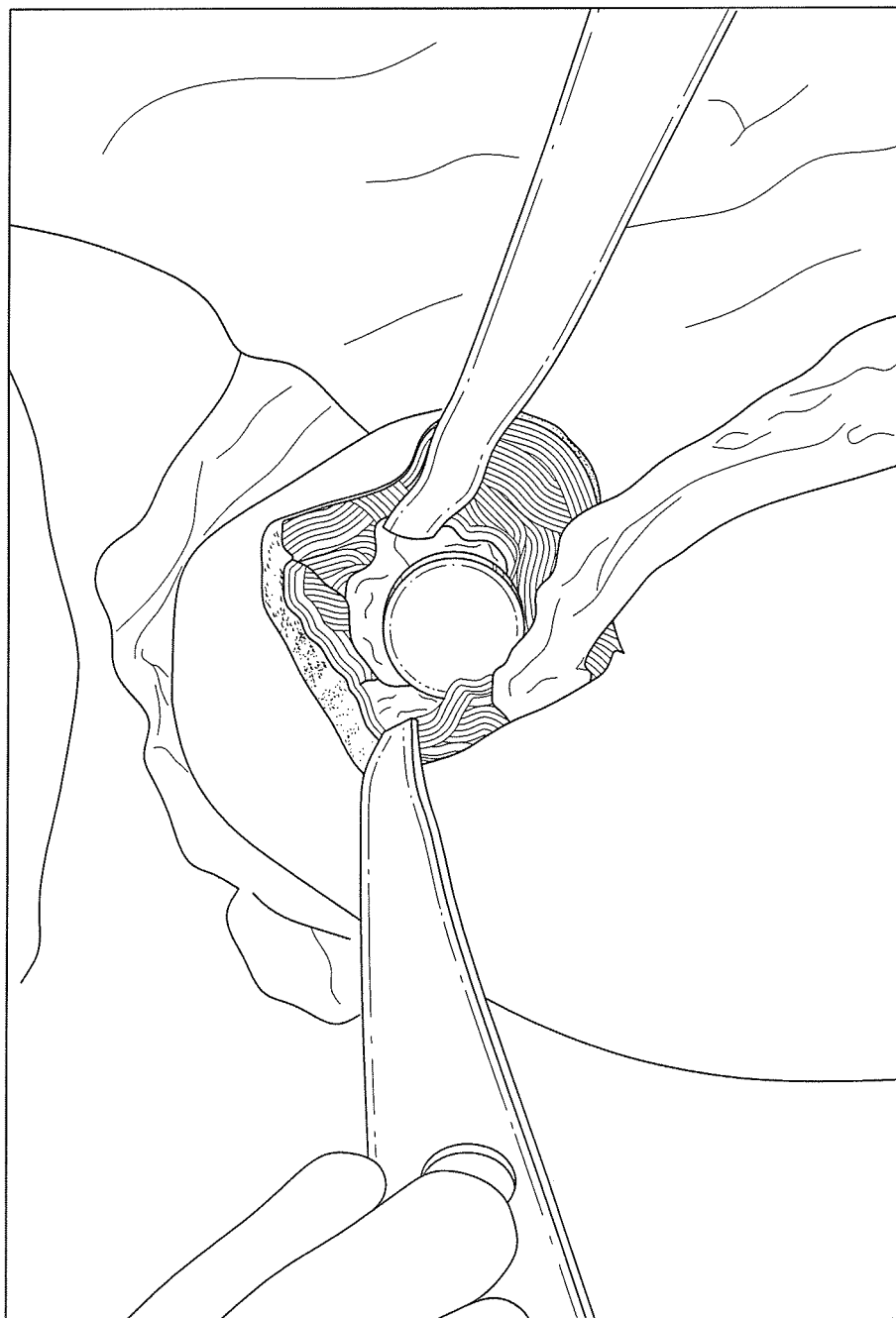
FIGS. 21, 22, and 23 are photographs showing the inset circular glenoid implant of the invention implanted in the glenoid of a patient.
Figure 22:
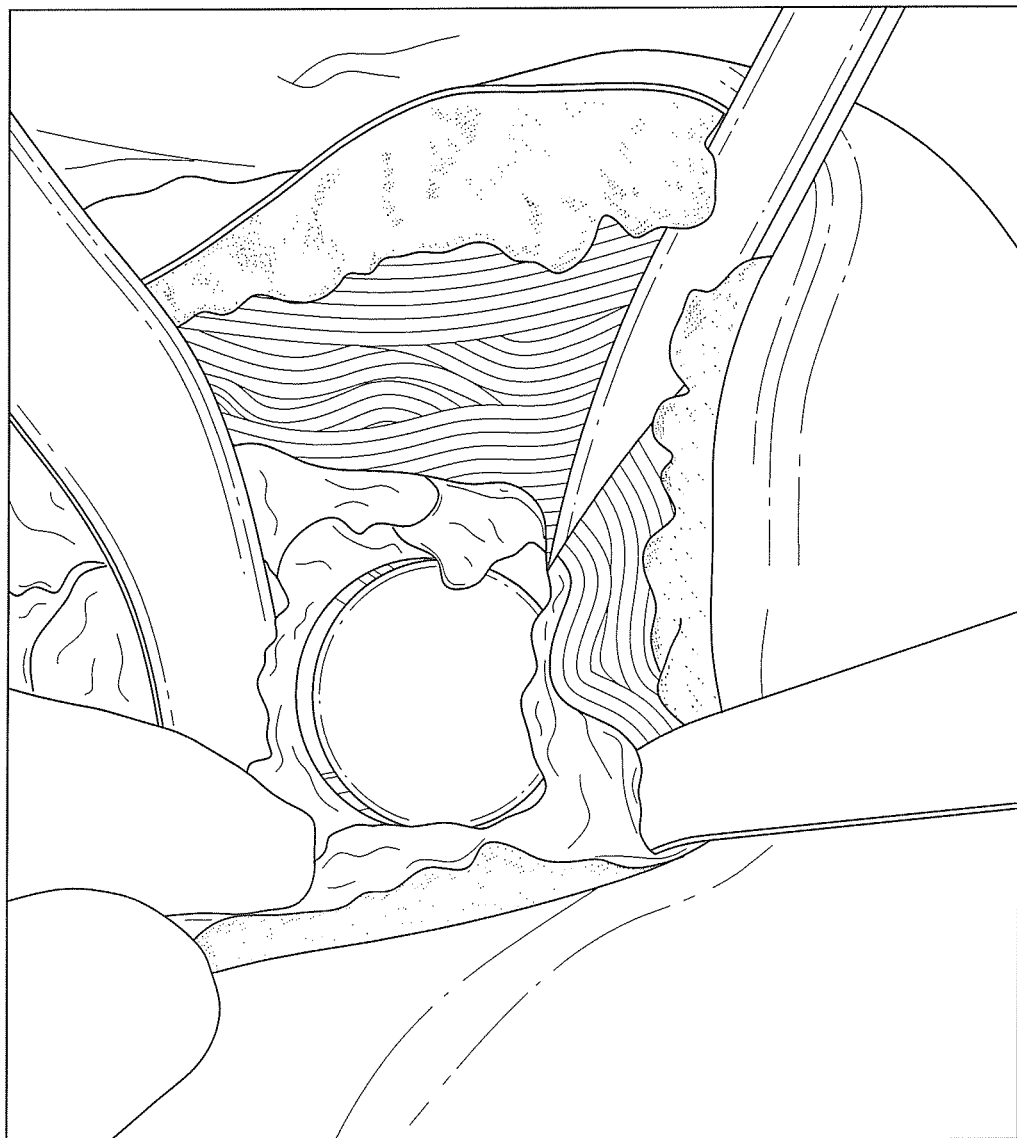
Figure 23:
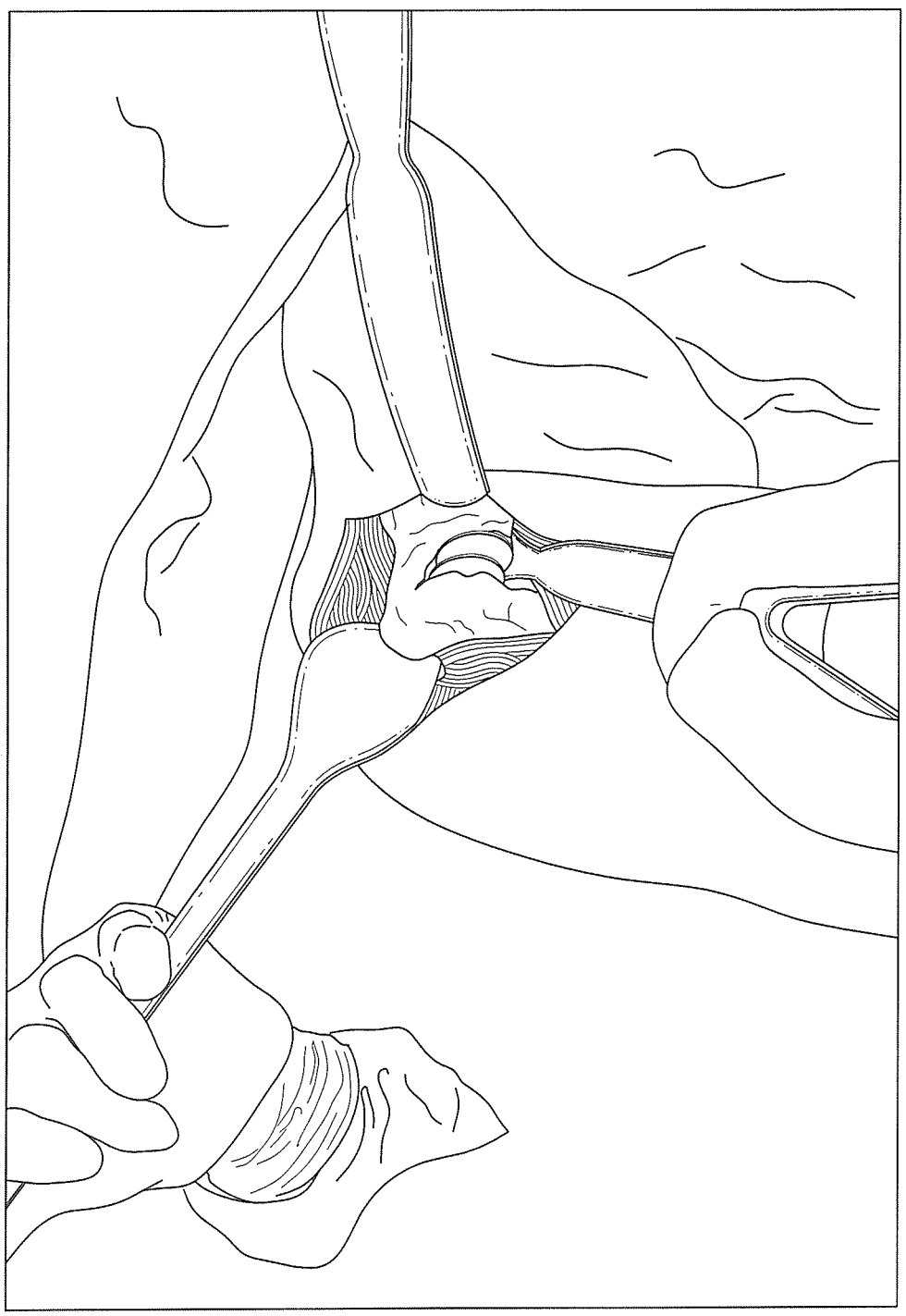
Figure 24:
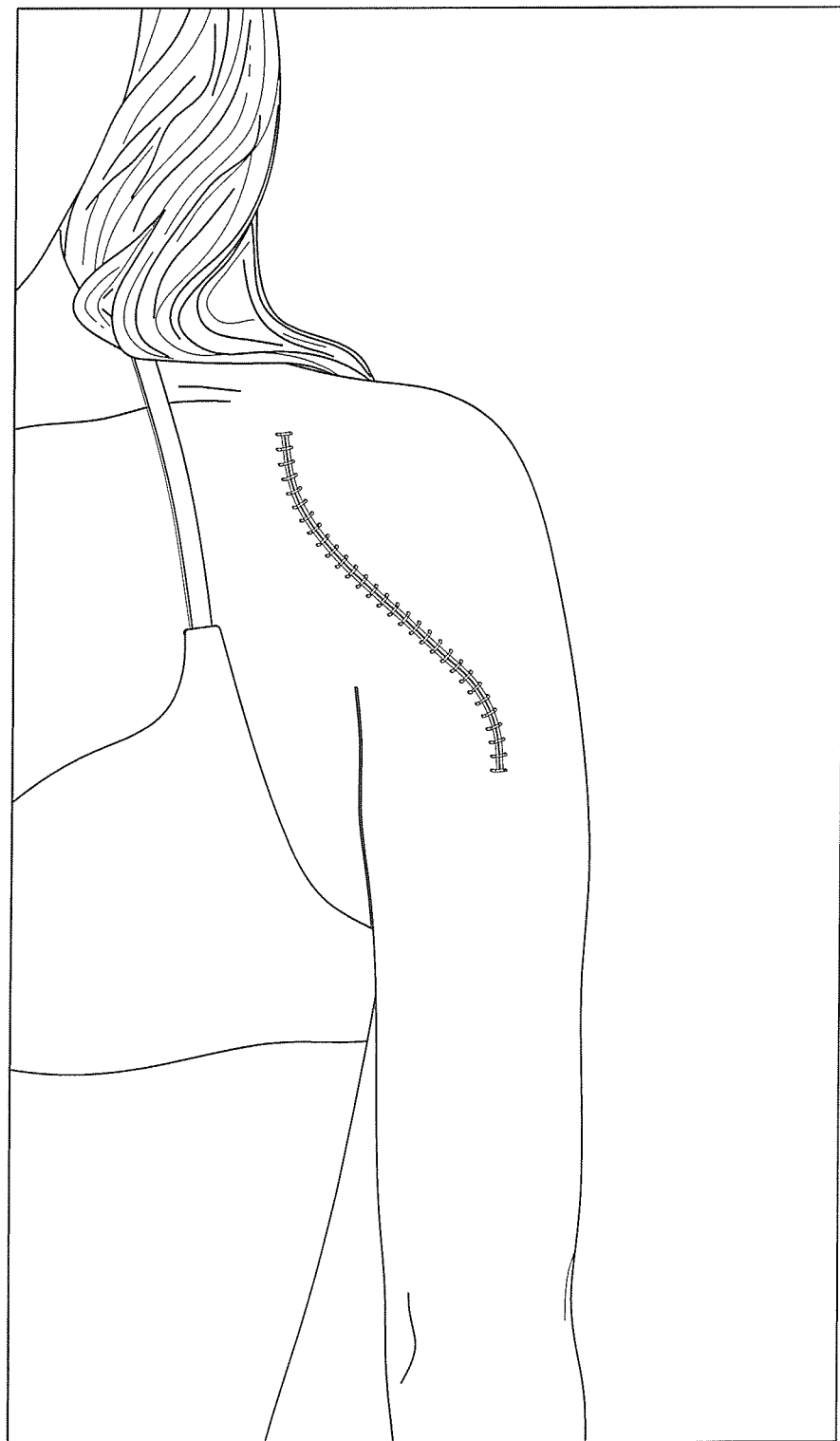
FIG. 24 is a photograph showing the 15 cm incision from a typical prior art total shoulder replacement surgery.
Figure 25:
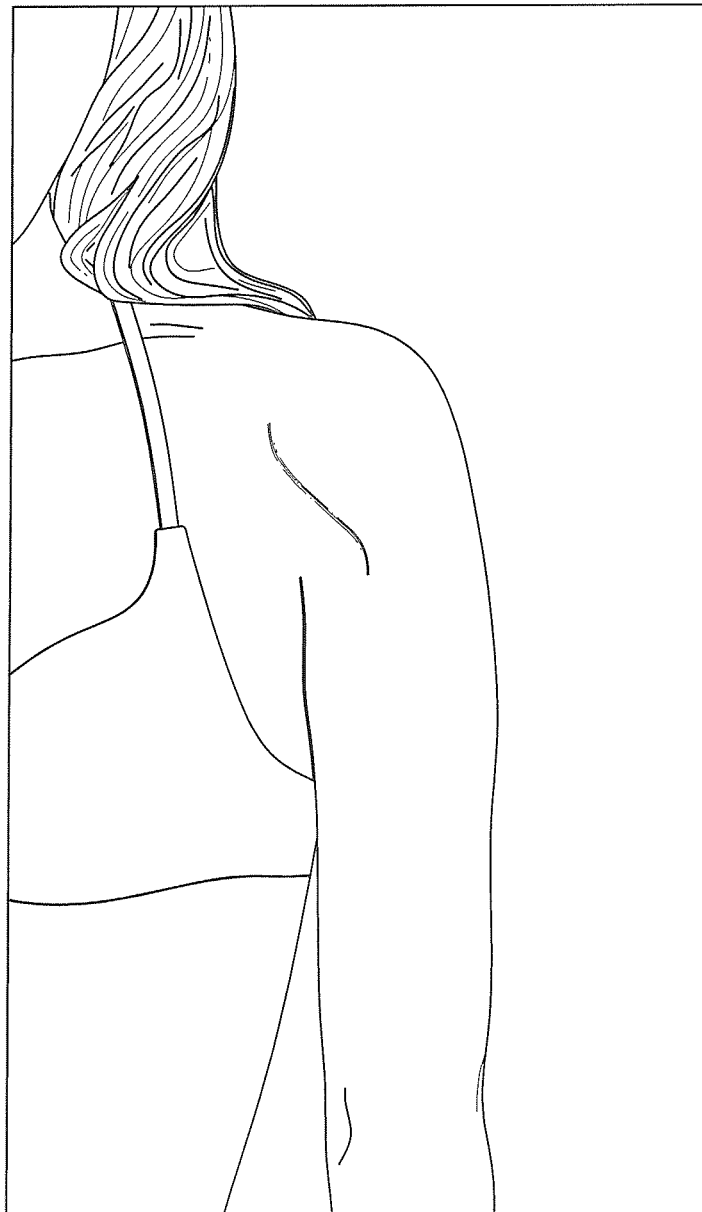
FIG. 25 is a photograph showing the 9 cm incision from the "mini-incision" total shoulder replacement surgery of the invention.

This surgery was performed through the "mini-incision total shoulder technique" described above. FIG. 25 shows the surgical incision 4 weeks post-operatively. FIG. 24, which shows a more typical total shoulder incision, clearly demonstrates the improved cosmetic appearance and reduced incision size achieved using the "mini-incision total shoulder technique" described above. FIGS. 21-23 are intraoperative pictures of the implanted inset glenoid prosthesis in this patient.

Example 2

An 81 year old woman presented with severe shoulder pain and stiffness. She had severe shoulder arthritis with medial wear causing glenoid bone loss. Her own assessment of shoulder function was 25% of normal (American Shoulder and Elbow Society validated outcome score [ASES score] was 25).

A total shoulder replacement using an inset glenoid implant prosthesis was performed. Two months after her surgery, the patient had no pain and exhibited improved function. Her own assessment of shoulder function was 70% of normal (American Shoulder and Elbow Society validated outcome score [ASES score] was 70).

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

What is claimed is:

1. A glenoid implant, comprising:
   a circular body, having a medial surface, an articulating surface, a peripheral edge, and a central axis;
   a peg on the medial surface, disposed concentrically on the central axis;
   wherein the medial surface extends radially outwardly to become a portion of the peripheral edge, wherein the portion of peripheral edge is concentric to and surrounds the peg; and
   a channel located on the peripheral edge and separating the portion of the peripheral edge that becomes the medial surface from a remaining portion of the peripheral edge, wherein the channel extends circumferentially around the peripheral edge and wherein the channel is concentric with the center of the circular body; and
   wherein a diameter of the circular body between the channel and the articulating surface is larger than a diameter of the circular body at the channel.

2. The glenoid implant of claim 1, wherein the portion of the peripheral edge is circular.

3. The glenoid implant of claim 1, wherein the portion of the peripheral edge is continuous.

4. The glenoid implant of claim 1, wherein the portion of the peripheral edge is aligned with the remaining portion of the peripheral edge.

5. The glenoid implant of claim 1, wherein a medial surface of the portion of the peripheral edge is flat.

6. The glenoid implant of claim 1, further comprising an annular fin located on the peg.

7. A glenoid implant as in claim 1, wherein the circular body has a first thickness measured in the axial direction at a first point on the peripheral edge, and a second thickness measured in the axial direction at a second point on the peripheral edge spaced apart from the first point by 180 degrees, and the first thickness is substantially equal to the second thickness.

8. A glenoid implant as in claim 1, wherein the circular body has a first thickness measured in the axial direction at a first point on the peripheral edge, and a second thickness measured in the axial direction at a second point on the peripheral edge spaced apart from the first point by 180 degrees, and wherein the first thickness is at least about 125% of the second thickness.

9. A glenoid implant as in claim 1, wherein the circular body has a first thickness measured in the axial direction at a first point on the peripheral edge, and a second thickness measured in the axial direction at a second point on the peripheral edge spaced apart from the first point by 180 degrees, and wherein the first thickness is at least about 150% of the second thickness.

10. A glenoid implant as in claim 1, wherein the circular body has a first thickness measured in the axial direction at a first point on the peripheral edge, and a second thickness measured in the axial direction at a second point on the peripheral edge spaced apart from the first point by 180 degrees, and wherein the first thickness is at least about 200% of the second thickness.

* * * * *